(12) United States Patent
Eshel et al.

(10) Patent No.: US 10,488,644 B2
(45) Date of Patent: Nov. 26, 2019

(54) METHODS AND APPARATUS FOR DETECTING AN ENTITY IN A BODILY SAMPLE

(71) Applicant: S.D. SIGHT DIAGNOSTICS LTD, Tel Aviv (IL)

(72) Inventors: Yochay Shlomo Eshel, Sde Warburg (IL); Natalie Lezmy, Rishon Lezion (IL); Dan Gluck, Kadima (IL); Arnon Houri Yafin, Jerusalem (IL); Joseph Joel Pollak, Neve Daniel (IL)

(73) Assignee: S.D. Sight Diagnostics Ltd., Tel Aviv (IL)

(*) Notice: Subject to any disclaimer, the term of this patent is extended or adjusted under 35 U.S.C. 154(b) by 116 days.

(21) Appl. No.: 15/760,782

(22) PCT Filed: Sep. 15, 2016

(86) PCT No.: PCT/IL2016/051025
§ 371 (c)(1),
(2) Date: Mar. 16, 2018

(87) PCT Pub. No.: WO2017/046799
PCT Pub. Date: Mar. 23, 2017

(65) Prior Publication Data
US 2018/0246313 A1    Aug. 30, 2018

Related U.S. Application Data

(60) Provisional application No. 62/219,889, filed on Sep. 17, 2015.

(51) Int. Cl.
*G02B 21/36* (2006.01)
*G06T 7/00* (2017.01)
(Continued)

(52) U.S. Cl.
CPC ....... *G02B 21/367* (2013.01); *G01N 21/8851* (2013.01); *G06K 9/00134* (2013.01);
(Continued)

(58) Field of Classification Search
CPC ........ G06T 7/0012; G06T 2207/30024; G06K 9/00127; G06K 9/0014; G06K 9/00147;
(Continued)

(56) References Cited

U.S. PATENT DOCUMENTS

| 3,603,156 A | 9/1971 | Konkol | 3/425.4 |
| 3,676,076 A | 7/1972 | Grady | 23/292 |

(Continued)

FOREIGN PATENT DOCUMENTS

| CA | 2655024 C | 11/2014 |
| CN | 101403650 B | 6/2010 |

(Continued)

OTHER PUBLICATIONS

Communication dated Feb. 22, 2018, issued by the United States Patent and Trademark Office in the prosecution of U.S. Appl. No. 14/369,251.

(Continued)

*Primary Examiner* — Andrew W Johns
(74) *Attorney, Agent, or Firm* — Sughrue Mion, PLLC

(57) ABSTRACT

Apparatus and methods are described including a microscope system (11) configured to acquire one or more microscope images of a bodily sample, an output device (34), and at least one computer processor (28). The computer processor identifies, in the one or more images, at least one element as being a pathogen candidate, and extracts, from the one or more images, at least one candidate-informative feature associated with the pathogen candidate. The compute processor extracts, from the one or more images, at least one sample-informative feature that is indicative of contextual (Continued)

information related to the bodily sample. The computer processor classifies a likelihood of the bodily sample being infected with a pathogenic infection, by processing the candidate-informative feature in combination with the sample-informative feature, and generates an output upon the output device, in response thereto. Other applications are also described.

27 Claims, 3 Drawing Sheets

(51) Int. Cl.
*G01N 21/88* (2006.01)
*G06K 9/00* (2006.01)

(52) U.S. Cl.
CPC ........ *G06K 9/00147* (2013.01); *G06T 7/0012* (2013.01); *G01N 2021/8887* (2013.01); *G06T 2207/10056* (2013.01); *G06T 2207/30024* (2013.01); *G06T 2207/30101* (2013.01)

(58) Field of Classification Search
CPC ...... G06K 9/46; G06K 9/4671; G02B 21/365; G02B 21/367
See application file for complete search history.

(56) References Cited

U.S. PATENT DOCUMENTS

| | | |
|---|---|---|
| 3,786,184 A | 1/1974 | Pieters ............................ 178/7.2 |
| 3,916,205 A | 10/1975 | Kleinerman ................... 250/461 |
| 3,967,056 A | 6/1976 | Yata et al. ...................... 178/7.2 |
| 4,076,419 A | 2/1978 | Kleker ............................ 356/39 |
| 4,209,548 A | 6/1980 | Bacus ............................... 427/2 |
| 4,350,884 A | 9/1982 | Vollath .......................... 250/204 |
| 4,454,235 A | 6/1984 | Johnson ........................ 436/536 |
| 4,494,479 A | 1/1985 | Drury et al. .................. 118/120 |
| 4,580,895 A | 4/1986 | Patel ............................... 356/39 |
| 4,700,298 A | 10/1987 | Palcic et al. .................. 364/414 |
| 4,761,381 A | 8/1988 | Blatt et al. .................... 436/165 |
| 4,774,192 A | 9/1988 | Terminiello et al. ......... 436/530 |
| 4,803,352 A | 2/1989 | Bierleutgeb .................. 205/201 |
| 4,849,340 A | 7/1989 | Oberhardt ....................... 435/13 |
| 4,851,330 A | 7/1989 | Kohne ............................. 435/6 |
| 4,902,101 A | 2/1990 | Fujihara et al. .............. 350/320 |
| 5,001,067 A | 3/1991 | Coleman et al. ............... 436/63 |
| 5,064,282 A | 11/1991 | Curtis ............................. 356/40 |
| 5,229,265 A | 7/1993 | Tometsko ......................... 435/6 |
| 5,300,779 A | 4/1994 | Hillman et al. .............. 250/341 |
| 5,331,958 A | 7/1994 | Oppenheimer ............... 128/633 |
| 5,430,542 A | 7/1995 | Shepherd ...................... 350/246 |
| 5,470,751 A | 11/1995 | Sakata et al. .................. 436/63 |
| 5,663,057 A | 9/1997 | Drocourt et al. ............ 435/40.5 |
| 5,672,861 A | 9/1997 | Fairley et al. ............... 250/201.3 |
| 5,674,457 A | 10/1997 | Williamsson et al. ....... 422/102 |
| 5,745,804 A | 4/1998 | Iwane ............................. 396/93 |
| 5,782,770 A | 7/1998 | Mooradian et al. .......... 600/476 |
| 5,834,217 A | 11/1998 | Levine et al. ............... 435/7.24 |
| 5,932,872 A | 8/1999 | Price ............................. 50/201.3 |
| 5,948,686 A | 9/1999 | Wardlaw ........................ 436/63 |
| 5,985,595 A | 11/1999 | Krider et al. ................... 435/34 |
| 6,005,964 A | 12/1999 | Reid et al. .................... 382/133 |
| 6,027,695 A | 2/2000 | Oldenburg et al. .......... 422/102 |
| 6,064,474 A | 5/2000 | Lee et al. ....................... 356/39 |
| 6,074,879 A | 6/2000 | Zelmanovic et al. .......... 436/10 |
| 6,101,404 A | 8/2000 | Yoon et al. ................... 600/310 |
| 6,262,798 B1 | 7/2001 | Shepherd et al. .............. 356/39 |
| 6,320,979 B1 | 11/2001 | Melen .......................... 382/154 |
| 6,350,613 B1 | 2/2002 | Wardlaw et al. ............... 436/10 |
| 6,448,024 B1 | 9/2002 | Bruegger ........................ 435/13 |
| 6,554,788 B1 | 4/2003 | Hunley et al. ............... 604/4.01 |
| 6,555,421 B2 | 4/2003 | Matsuyama et al. ......... 438/164 |
| 6,582,964 B1 | 6/2003 | Samsoondar et al. .......... 436/67 |
| 6,611,777 B2 | 8/2003 | Samsoondar ................ 102/104 |
| 6,632,681 B1 | 10/2003 | Chu .............................. 436/178 |
| 6,658,143 B2 | 12/2003 | Hansen et al. ............... 382/133 |
| 6,664,528 B1 | 12/2003 | Cartlidge et al. .......... 250/208.1 |
| 6,711,516 B2 | 3/2004 | Samsoondar .................. 702/86 |
| 6,799,119 B1 | 9/2004 | Voorhees et al. .............. 702/19 |
| 6,819,408 B1 | 11/2004 | Scrivens et al. ............... 356/39 |
| 6,831,733 B2 | 12/2004 | Pettersson et al. ............ 356/39 |
| 6,834,237 B2 | 12/2004 | Noergaard et al. ............ 702/19 |
| 6,836,559 B2 | 12/2004 | Abdel-Fattah et al. ...... 382/134 |
| 6,842,233 B2 | 1/2005 | Narisada et al. ............... 356/39 |
| 6,866,823 B2 | 3/2005 | Wardlaw ................... 422/82.05 |
| 6,872,930 B2 | 3/2005 | Cartlidge et al. .......... 250/208.1 |
| 6,898,451 B2 | 5/2005 | Wuori ........................... 600/322 |
| 6,903,323 B2 | 6/2005 | Cartlidge et al. .......... 250/208.1 |
| 6,929,953 B1 | 8/2005 | Wardlaw ........................ 436/63 |
| 6,949,384 B2 | 9/2005 | Samsoondar .................. 436/66 |
| 6,955,872 B2 | 10/2005 | Maples et al. ................... 435/4 |
| 6,956,650 B2 | 10/2005 | Boas et al. ................... 356/432 |
| 6,989,891 B2 | 1/2006 | Braig et al. .................... 356/39 |
| 7,027,628 B2 | 4/2006 | Gagnon et al. .............. 382/128 |
| 7,030,351 B2 | 4/2006 | Wasserman et al. ....... 250/201.3 |
| 7,034,883 B1 | 4/2006 | Rosenqvist .................. 348/345 |
| 7,105,795 B2 | 9/2006 | Cartlidge et al. .......... 250/208.1 |
| 7,132,636 B1 | 11/2006 | Cartlidge et al. .......... 250/208.1 |
| 7,133,547 B2 | 11/2006 | Marcelpoil et al. .......... 382/129 |
| 7,151,246 B2 | 12/2006 | Fein et al. ................... 250/208.1 |
| 7,155,049 B2 | 12/2006 | Wetzel et al. ................ 382/133 |
| 7,248,716 B2 | 7/2007 | Fein et al. .................... 382/100 |
| 7,274,810 B2 | 9/2007 | Reeves et al. ............... 382/128 |
| 7,283,217 B2 | 10/2007 | Ikeuchi et al. ................. 356/39 |
| 7,288,751 B2 | 10/2007 | Cartlidge et al. .......... 250/208.1 |
| 7,305,109 B1 | 12/2007 | Gagnon et al. .............. 382/128 |
| 7,324,694 B2 | 1/2008 | Chapoulaud et al. ........ 382/224 |
| 7,329,537 B2 | 2/2008 | Qiu ............................. 435/288.3 |
| 7,338,168 B2 | 3/2008 | Cartlidge et al. ............. 351/206 |
| 7,344,890 B2 | 3/2008 | Perez et al. .................... 436/63 |
| 7,346,205 B2 | 3/2008 | Walker, Jr. ................... 382/133 |
| 7,369,696 B2 | 5/2008 | Arini et al. .................. 382/133 |
| 7,385,168 B2 | 6/2008 | Cartlidge et al. .......... 250/208.1 |
| 7,411,680 B2 | 8/2008 | Chang et al. ................ 356/432 |
| 7,417,213 B2 | 8/2008 | Krief et al. ................. 250/208.1 |
| 7,425,421 B2 | 9/2008 | Dertinger ................... 435/7.25 |
| 7,439,478 B2 | 10/2008 | Cartlidge et al. .......... 250/208.1 |
| 7,450,223 B2 | 11/2008 | Ikeuchi et al. ................. 356/39 |
| 7,450,762 B2 | 11/2008 | Morell ......................... 328/199 |
| 7,460,222 B2 | 12/2008 | Kalveram et al. ............ 356/244 |
| 7,490,085 B2 | 2/2009 | Walker et al. ................ 707/10 |
| 7,493,219 B1 | 2/2009 | Qi et al. ......................... 702/26 |
| 7,580,120 B2 | 8/2009 | Hamada et al. ............... 356/73 |
| 7,599,893 B2 | 10/2009 | Sapir et al. .................... 706/12 |
| 7,601,938 B2 | 10/2009 | Cartlidge et al. .......... 250/208.1 |
| 7,602,954 B2 | 10/2009 | Marcelpoil et al. .......... 382/129 |
| 7,605,356 B2 | 10/2009 | Krief et al. ................. 250/208.1 |
| 7,609,369 B2 | 10/2009 | Simon-Lopez ................ 356/39 |
| 7,630,063 B2 | 12/2009 | Padmanabhan et al. ...... 356/39 |
| 7,633,604 B2 | 12/2009 | Ikeuchi et al. ................. 356/39 |
| 7,638,748 B2 | 12/2009 | Krief et al. ................. 250/208.1 |
| 7,663,738 B2 | 2/2010 | Johansson ...................... 356/39 |
| 7,668,362 B2 | 2/2010 | Olson et al. .................. 382/133 |
| 7,692,131 B2 | 4/2010 | Fein et al. ................... 250/208.1 |
| 7,697,764 B2 | 4/2010 | Kataoka ....................... 382/225 |
| 7,702,181 B2 | 4/2010 | Gouch ......................... 382/284 |
| 7,706,862 B2 | 4/2010 | Alfano et al. ................ 600/473 |
| 7,713,474 B2 | 5/2010 | Schulman et al. ............. 422/58 |
| 7,747,153 B2 | 6/2010 | Ibaraki ........................... 396/55 |
| 7,765,069 B2 | 7/2010 | Ostoich et al. ................ 702/19 |
| 7,777,869 B2 | 8/2010 | Nerin et al. .................... 356/39 |
| 7,787,109 B2 | 8/2010 | Dosmann et al. ............. 356/39 |
| 7,863,552 B2 | 1/2011 | Cartlidge et al. .......... 250/208.1 |
| 7,869,009 B2 | 1/2011 | Dosmann et al. ............. 356/39 |
| 7,894,047 B2 | 2/2011 | Hamada et al. ............... 356/39 |
| 7,911,617 B2 | 3/2011 | Padmanabhan et al. ..... 356/450 |
| 7,925,070 B2 | 4/2011 | Sumida et al. ............... 382/134 |
| 7,929,121 B2 | 4/2011 | Wardlaw et al. ............... 356/39 |
| 7,933,435 B2 | 4/2011 | Hunter et al. ................ 382/128 |
| 7,936,913 B2 | 5/2011 | Nordell et al. ............... 382/134 |
| 7,951,599 B2 | 5/2011 | Levine et al. .................. 436/70 |
| 7,995,200 B2 | 8/2011 | Matsumoto ................... 356/244 |

(56) References Cited

U.S. PATENT DOCUMENTS

| | | | |
|---|---|---|---|
| 7,998,435 B2 | 8/2011 | Reed | 422/507 |
| 8,000,511 B2 | 8/2011 | Perz | 382/128 |
| 8,044,974 B2 | 10/2011 | Sumida et al. | 345/629 |
| 8,045,782 B2 | 10/2011 | Li et al. | 382/133 |
| 8,055,471 B2 | 11/2011 | Qi et al. | 702/180 |
| 8,064,680 B2 | 11/2011 | Ramoser et al. | 382/134 |
| 8,077,296 B2 | 12/2011 | Wardlaw et al. | 356/39 |
| 8,081,303 B2 | 12/2011 | Levine et al. | 356/39 |
| 8,105,554 B2 | 1/2012 | Kanigan et al. | 422/504 |
| 8,125,643 B2 | 2/2012 | Hansen et al. | 356/436 |
| 8,131,035 B2 | 3/2012 | Grady et al. | 382/128 |
| 8,131,052 B2 | 3/2012 | Alexandrov | 382/133 |
| 8,150,114 B2 | 4/2012 | Svanberg et al. | 382/128 |
| 8,154,713 B2 | 4/2012 | Simon-Lopez | 356/39 |
| 8,165,385 B2 | 4/2012 | Reeves et al. | 382/154 |
| 8,175,353 B2 | 5/2012 | Westphal et al. | 382/128 |
| 8,184,273 B2 | 5/2012 | Dosmann et al. | 356/39 |
| 8,216,832 B2 | 7/2012 | Battrell et al. | 435/309.1 |
| 8,224,058 B2 | 7/2012 | Lindberg et al. | 382/133 |
| 8,269,954 B2 | 9/2012 | Levine et al. | 356/39 |
| 8,280,134 B2 | 10/2012 | Hoyt | 382/128 |
| 8,310,659 B2 | 11/2012 | Wardlaw et al. | 356/39 |
| 8,320,655 B2 | 11/2012 | Sarachan et al. | 382/133 |
| 8,331,642 B2 | 12/2012 | Zerfass et al. | 382/134 |
| 8,339,586 B2 | 12/2012 | Zahniser et al. | 356/39 |
| 8,345,227 B2 | 1/2013 | Zahniser et al. | 356/40 |
| 8,351,676 B2 | 1/2013 | Dai et al. | 382/133 |
| 8,363,221 B2 | 1/2013 | Hansen et al. | 356/436 |
| 8,379,944 B2 | 2/2013 | Grady et al. | 382/128 |
| 8,428,331 B2 | 4/2013 | DiMarzio et al. | 382/133 |
| 8,432,392 B2 | 4/2013 | Kim et al. | 345/419 |
| 8,477,294 B2 | 7/2013 | Zahniser et al. | 356/39 |
| 8,481,303 B2 | 7/2013 | Faris et al. | 435/289.1 |
| 8,488,111 B2 | 7/2013 | Zahniser et al. | 356/39 |
| 8,491,499 B2 | 7/2013 | Choi et al. | 600/576 |
| 8,526,704 B2 | 9/2013 | Dobbe | 382/134 |
| 8,570,496 B2 | 10/2013 | Chen | G01N 33/49 |
| 8,582,924 B2 | 11/2013 | De La Torre-Bueno et al. | 382/305 |
| 8,638,427 B2 | 1/2014 | Wardlaw et al. | G01N 33/49 |
| 8,712,142 B2 | 4/2014 | Rajpoot et al. | 382/134 |
| 8,736,824 B2 | 5/2014 | Matsui et al. | G01N 33/49 |
| 8,744,165 B2 | 6/2014 | Liu et al. | 382/133 |
| 8,778,687 B2 | 7/2014 | Levine et al. | G01N 33/80 |
| 8,792,693 B2 | 7/2014 | Satish et al. | G06K 9/00 |
| 8,849,024 B2 | 9/2014 | Shinoda et al. | G06K 9/0014 |
| 8,873,827 B2 | 10/2014 | McCulloch et al. | 382/134 |
| 8,877,458 B2 | 11/2014 | Maurer | C12Q 1/04 |
| 8,878,923 B2 | 11/2014 | Henderson et al. | 348/79 |
| 8,885,154 B2 | 11/2014 | Wardlaw et al. | G06T 7/0012 |
| 8,885,912 B2 | 11/2014 | Sui | G06F 19/24 |
| 8,922,761 B2 | 12/2014 | Zahniser et al. | G06K 9/00127 |
| 8,942,458 B2 | 1/2015 | Takahashi et al. | G01N 15/147 |
| 8,964,171 B2 | 2/2015 | Zahniser et al. | G01N 15/1475 |
| 8,994,930 B2 | 3/2015 | Levine et al. | G01N 33/5091 |
| 9,012,868 B2 | 4/2015 | Courtney et al. | G01N 21/6458 |
| 9,041,792 B2 | 5/2015 | Van Leeuwen et al. | A63B 43/02 |
| 9,046,473 B2 | 6/2015 | Levine et al. | G01N 21/21 |
| 9,050,595 B2 | 6/2015 | Miller et al. | B01L 3/50273 |
| 9,186,843 B2 | 11/2015 | Chan et al. | B29C 59/021 |
| 9,240,043 B2 | 1/2016 | Christiansen et al. | G06T 7/0012 |
| 9,329,129 B2 | 5/2016 | Pollak et al. | G01N 21/6428 |
| 9,404,852 B2 | 8/2016 | Braig et al. | G01N 21/35 |
| 9,470,609 B2 | 10/2016 | Wimberger-Friedl et al. | G01N 1/2813 |
| 9,477,875 B2 | 10/2016 | Ohya et al. | G06K 9/0014 |
| 9,522,396 B2 | 12/2016 | Bachelet et al. | B01L 3/502715 |
| 9,588,033 B2 | 3/2017 | Zahniser et al. | G01N 15/0227 |
| 9,820,990 B2 | 11/2017 | Pak et al. | A61K 31/5415 |
| 9,934,571 B2 | 4/2018 | Ozaki et al. | G06T 7/0042 |
| 10,061,972 B2 | 8/2018 | Champlin et al. | G06K 9/0014 |
| 10,093,957 B2 | 10/2018 | Pollak et al. | C12Q 1/04 |
| 10,176,565 B2 | 1/2019 | Greenfield et al. | G06T 7/0012 |
| 2002/0009711 A1 | 1/2002 | Wada et al. | 435/4 |
| 2002/0028158 A1 | 3/2002 | Wardlaw | 422/82.05 |
| 2002/0028471 A1 | 5/2002 | Oberhardt | 435/7.21 |
| 2003/0017085 A1 | 1/2003 | Kercso et al. | 422/104 |
| 2003/0161514 A1 | 8/2003 | Curry | 382/128 |
| 2003/0170613 A1 | 9/2003 | Straus | 435/5 |
| 2003/0197925 A1 | 10/2003 | Hamborg | 359/383 |
| 2003/0224522 A1 | 12/2003 | de Jong et al. | 435/458 |
| 2003/0227612 A1 | 12/2003 | Fein et al. | 356/39 |
| 2003/0227673 A1 | 12/2003 | Nakagawa | 359/380 |
| 2003/0231971 A1 | 12/2003 | Klassen | 418/195 |
| 2004/0132171 A1 | 7/2004 | Rule et al. | 435/287.2 |
| 2004/0170312 A1 | 9/2004 | Soenksen | 382/133 |
| 2004/0185447 A1 | 9/2004 | Maples et al. | 435/6 |
| 2004/0218804 A1 | 11/2004 | Affleck et al. | 382/141 |
| 2004/0240050 A1 | 12/2004 | Ogihara | 359/382 |
| 2004/0241677 A1 | 12/2004 | Lin et al. | 435/6 |
| 2005/0089208 A1 | 4/2005 | Dong et al. | 382/133 |
| 2005/0109959 A1 | 5/2005 | Wasserman et al. | 250/559.19 |
| 2005/0175992 A1 | 8/2005 | Aberl et al. | 435/5 |
| 2005/0286800 A1 | 12/2005 | Gouch | 382/284 |
| 2006/0003458 A1 | 1/2006 | Golovchenko et al. | 436/86 |
| 2006/0045505 A1 | 3/2006 | Zeineh et al. | 396/89 |
| 2006/0063185 A1 | 3/2006 | Vannier | 435/6 |
| 2006/0187442 A1 | 8/2006 | Chang et al. | 356/39 |
| 2006/0190226 A1 | 8/2006 | Jojic et al. | 703/11 |
| 2006/0222567 A1 | 10/2006 | Kloepfer et al. | 422/68.1 |
| 2006/0223052 A1 | 10/2006 | MacDonald et al. | 435/5 |
| 2006/0223165 A1 | 10/2006 | Chang et al. | 435/287.1 |
| 2007/0054350 A1 | 3/2007 | Walker, Jr. | 435/34 |
| 2007/0243117 A1 | 10/2007 | Wardlaw | 422/255 |
| 2007/0250301 A1 | 10/2007 | Vaisberg et al. | 703/11 |
| 2007/0252984 A1 | 11/2007 | Van Beek et al. | 356/311 |
| 2008/0020128 A1 | 1/2008 | van Ryper et al. | 427/2.11 |
| 2008/0059135 A1 | 3/2008 | Murugkar et al. | 703/11 |
| 2008/0118399 A1 | 5/2008 | Fleming | 422/68.1 |
| 2008/0187466 A1 | 8/2008 | Wardlaw | 422/102 |
| 2008/0212069 A1 | 9/2008 | Goldberg et al. | 356/36 |
| 2008/0260369 A1 | 10/2008 | Ibaraki | 396/55 |
| 2008/0273776 A1 | 11/2008 | Krief et al. | 382/128 |
| 2008/0305514 A1 | 12/2008 | Alford et al. | 435/34 |
| 2009/0066934 A1 | 3/2009 | Gao et al. | 356/73 |
| 2009/0075324 A1 | 3/2009 | Pettersson | 435/39 |
| 2009/0128618 A1 | 5/2009 | Fahn et al. | 348/39 |
| 2009/0185734 A1 | 7/2009 | Lindberg et al. | 382/133 |
| 2009/0191098 A1 | 7/2009 | Beard et al. | 422/100 |
| 2009/0195688 A1 | 8/2009 | Henderson et al. | 348/345 |
| 2009/0213214 A1 | 8/2009 | Yamada | 348/80 |
| 2009/0258347 A1 | 10/2009 | Scott | 435/6 |
| 2009/0269799 A1 | 10/2009 | Winkelman et al. | 435/29 |
| 2009/0269854 A1 | 11/2009 | Wiesinger-Mayr et al. | 506/8 |
| 2010/0068747 A1 | 3/2010 | Herrenknecht | 435/29 |
| 2010/0112631 A1 | 5/2010 | Hur et al. | 435/39 |
| 2010/0120129 A1 | 5/2010 | Amshey et al. | 435/270 |
| 2010/0136556 A1 | 6/2010 | Friedberger et al. | 435/6 |
| 2010/0136570 A1 | 6/2010 | Goldberg et al. | 435/6 |
| 2010/0152054 A1 | 6/2010 | Love et al. | 506/9 |
| 2010/0157086 A1 | 6/2010 | Segale et al. | 48/222.1 |
| 2010/0172020 A1 | 7/2010 | Price et al. | 359/381 |
| 2010/0254596 A1 | 10/2010 | Xiong et al. | 382/159 |
| 2010/0256918 A1 | 10/2010 | Chen et al. | 702/19 |
| 2010/0265323 A1 | 10/2010 | Perz | 348/79 |
| 2010/0295998 A1 | 11/2010 | Sakai et al. | 348/700 |
| 2010/0300563 A1 | 12/2010 | Ramunas et al. | 137/565.01 |
| 2011/0001102 A1 | 1/2011 | Kahlman | 348/222.1 |
| 2011/0009163 A1 | 1/2011 | Fletcher et al. | 455/556.1 |
| 2011/0030458 A1 | 2/2011 | Park et al. | 73/64.56 |
| 2011/0102571 A1 | 5/2011 | Yoneyama | 348/79 |
| 2011/0123398 A1 | 5/2011 | Carrilho et al. | 422/68.1 |
| 2011/0144480 A1 | 6/2011 | Lu et al. | 600/424 |
| 2011/0149097 A1 | 6/2011 | Danuser et al. | 48/222.1 |
| 2011/0151502 A1 | 6/2011 | Kendall et al. | 435/39 |
| 2011/0178716 A1 | 7/2011 | Krockenberger et al. | 702/19 |
| 2011/0212486 A1 | 9/2011 | Yamada et al. | 435/40.5 |
| 2011/0249910 A1 | 10/2011 | Henderson et al. | 382/278 |
| 2011/0275111 A1 | 11/2011 | Pettigrew et al. | 435/29 |
| 2012/0002195 A1 | 1/2012 | Wu et al. | 356/213 |

(56) References Cited

U.S. PATENT DOCUMENTS

| | | | |
|---|---|---|---|
| 2012/0021951 A1 | 1/2012 | Hess et al. | 506/13 |
| 2012/0030618 A1 | 2/2012 | Leong et al. | 715/810 |
| 2012/0044342 A1 | 2/2012 | Hing et al. | 348/79 |
| 2012/0058504 A1 | 3/2012 | Li et al. | 435/29 |
| 2012/0092477 A1 | 4/2012 | Kawano et al. | 348/79 |
| 2012/0120221 A1 | 5/2012 | Dong et al. | 348/77 |
| 2012/0169863 A1 | 7/2012 | Bachelet et al. | 348/79 |
| 2012/0225446 A1 | 9/2012 | Wimberger-Friedl et al. | 435/29 |
| 2012/0312957 A1 | 12/2012 | Loney et al. | 250/201.3 |
| 2012/0320045 A1 | 12/2012 | Yao et al. | 345/419 |
| 2013/0023007 A1 | 1/2013 | Zahniser et al. | 435/34 |
| 2013/0078668 A1 | 3/2013 | Levine et al. | 435/34 |
| 2013/0130262 A1 | 5/2013 | Battrell et al. | B01L 3/50273 |
| 2013/0176551 A1 | 7/2013 | Wardlaw et al. | G01N 33/49 |
| 2013/0273968 A1 | 10/2013 | Rhoads et al. | H04M 1/0264 |
| 2013/0284924 A1 | 10/2013 | Mizuochi et al. | G01N 23/2206 |
| 2013/0290225 A1 | 10/2013 | Kamath et al. | 702/12 |
| 2014/0139625 A1 | 5/2014 | Mathuis et al. | 348/10 |
| 2014/0139630 A1 | 5/2014 | Kowalevicz | H04N 13/0203 |
| 2014/0186859 A1 | 7/2014 | Calderwood et al. | G01N 33/56911 |
| 2014/0205176 A1 | 7/2014 | Obrien et al. | G06K 9/00134 |
| 2014/0347459 A1 | 11/2014 | Greenfield et al. | G06T 7/0012 |
| 2015/0037806 A1 | 2/2015 | Pollak et al. | C12Q 1/68 |
| 2015/0278575 A1 | 10/2015 | Allano et al. | G06K 9/0014 |
| 2015/0302237 A1 | 10/2015 | Ohya et al. | G06K 9/0014 |
| 2015/0316477 A1 | 11/2015 | Pollak et al. | G01N 21/6428 |
| 2016/0208306 A1 | 7/2016 | Pollak et al. | C12Q 1/04 |
| 2016/0246046 A1 | 8/2016 | Yorav Raphael et al. | G02B 21/367 |
| 2016/0279633 A1 | 9/2016 | Bechelet et al. | B01L 3/502715 |
| 2017/0052110 A1 | 2/2017 | Malissek et al. | G01N 21/03 |
| 2017/0160185 A1 | 6/2017 | Minemura et al. | G01N 15/14 |
| 2017/0307496 A1 | 10/2017 | Zahniser et al. | G01N 15/0227 |
| 2018/0246313 A1 | 8/2018 | Eshel et al. | G02B 21/367 |
| 2018/0296102 A1 | 10/2018 | Satish et al. | A61B 5/02042 |
| 2019/0002950 A1 | 1/2019 | Pollak et al. | C12Q 1/04 |

FOREIGN PATENT DOCUMENTS

| | | |
|---|---|---|
| EP | 0073551 A2 | 3/1983 |
| EP | 0479231 A1 | 4/1992 |
| EP | 1 381 229 A1 | 1/2004 |
| EP | 1698883 A1 | 9/2006 |
| EP | 2145684 A2 | 1/2010 |
| EP | 3001174 A1 | 3/2016 |
| GB | 2329014 A | 3/1999 |
| JP | 61-198204 A | 9/1986 |
| JP | H11-73903 A | 3/1999 |
| JP | 2000-199845 A | 7/2000 |
| JP | 2004-144526 A | 5/2004 |
| JP | 2004-257768 A | 9/2004 |
| JP | 2006-301270 A | 11/2006 |
| JP | 2007040814 A | 2/2007 |
| WO | 85/05446 A1 | 12/1985 |
| WO | 96/01438 A1 | 1/1996 |
| WO | 96/13615 A1 | 5/1996 |
| WO | 1996/012981 A1 | 5/1996 |
| WO | 00/06765 A1 | 2/2000 |
| WO | 00/52195 A1 | 9/2000 |
| WO | 2000/055572 A1 | 9/2000 |
| WO | 03/056327 A1 | 7/2003 |
| WO | 2003/073365 A1 | 9/2003 |
| WO | 03/081525 A1 | 10/2003 |
| WO | 2004/111610 A2 | 12/2004 |
| WO | 2005/121863 A1 | 12/2005 |
| WO | 2006/121266 A1 | 11/2006 |
| WO | 2008/063135 A1 | 5/2008 |
| WO | 2010/056740 A1 | 5/2010 |
| WO | 2010/116341 A1 | 10/2010 |
| WO | 2010/126903 A1 | 11/2010 |
| WO | 2011/076413 A1 | 6/2011 |
| WO | 2011/123070 A1 | 10/2011 |
| WO | 2011/143075 A2 | 11/2011 |
| WO | 2012/000102 A1 | 1/2012 |
| WO | 2012/030313 A1 | 3/2012 |
| WO | 2012/090198 A3 | 7/2012 |
| WO | 2012/154333 A1 | 11/2012 |
| WO | 2013/098821 A1 | 7/2013 |
| WO | 2014/159620 A1 | 10/2014 |
| WO | 2014/188405 A1 | 11/2014 |
| WO | 2015/001553 A1 | 1/2015 |
| WO | 2015/029032 A1 | 3/2015 |
| WO | 2016/030897 A1 | 3/2016 |
| WO | 2017/046799 A1 | 3/2017 |
| WO | 2017/168411 A1 | 10/2017 |
| WO | 2017/195205 A1 | 11/2017 |
| WO | 2017/195208 A1 | 11/2017 |
| WO | 2019/097387 A1 | 5/2019 |

OTHER PUBLICATIONS

Communication dated Mar. 23, 2018, issued by the Intellectual Property Office of India in co-pending Indian Application No. 4263/DELNP/2014.

An Office Action dated Jan. 10, 2018, which issued during the prosecution of U.S. Appl. No. 15/083,610.

Matcher, S. J., M. Cope, and D. T. Delpy. "Use of the water absorption spectrum to quantify tissue chromophore concentration changes in near-infrared spectroscopy." Physics in medicine and biology 39.1 (1994): 177.

Rappaz, Benjamin, et al. "Comparative study of human erythrocytes by digital holographic microscopy, confocal microscopy, and impedance volume analyzer." Cytometry Part A 73.10 (2008): 895-903.

Ross, Nicholas E., et al. "Automated image processing method for the diagnosis and classification of malaria on thin blood smears." Medical and Biological Engineering and Computing 44.5 (2006): 427-436.

Houri-Yafin, A., et al. "An enhanced computer vision platform for clinical diagnosis of malaria." Malar Control Elimin 5.138.10 (2016): 4172.

Ahirwar, Neetu, Sapnojit Pattnaik, and Bibhudendra Acharya. "Advanced image analysis based system for automatic detection and classification of malarial parasite in blood images." International Journal of Information Technology and Knowledge Management 5.1 (2012): 59-64.

An Office Action dated Aug. 4, 2017, which issued during the prosecution of U.S. Appl. No. 14/369,251.

An Office Action dated Jun. 13, 2017, which issued during the prosecution of U.S. Appl. No. 14/285,672.

An Office Action dated Jul. 11, 2017, which issued during the prosecution of U.S. Appl. No. 15/174,490.

Osibote, O. A., et al. "Automated focusing in bright-field microscopy for tuberculosis detection." Journal of microscopy 240.2 (2010): 155-163.

Shen, Feimo, Louis Hodgson, and Klaus Hahn. "Digital autofocus methods for automated microscopy." Methods in enzymology 414 (2006): 620-632.

Wu, Qiang, Fatima Merchant, and Kenneth Castleman. Microscope image processing. Chapter 16, "Autofocusing", pp. 441-467, Academic press, 2010.

Purwar, Yashasvi, et al. "Automated and unsupervised detection of malarial parasites in microscopic images." Malaria journal 10.1 (2011): 364.

Frean, John. "Microscopic determination of malaria parasite load: role of image analysis." Microscopy: Science, technology. Applications, and Education (2010): 862-866.

Price, Jeffrey H., and David A. Gough. "Comparison of phase—contrast and fluorescence digital autofocus for scanning microscopy." Cytometry 16.4 (1994): 283-297.

Vink, J. P.,etal. "An automatic vision based malaria diagnosis system."Journal of microscopy 250.3(2013): 166-178.b.

Chong, Shau Poh, Shilpa Pant, and Nanguang Chen. "Line-scan focal modulation microscopy for rapid imaging of thick biological

(56) References Cited

OTHER PUBLICATIONS specimens." S PIE/OS A/IEEE Asia Communications and Photonics. International Society for Optics and Photonics, 2011.
Yang, Ming, and Li Luo. "A rapid auto-focus method in automatic microscope." Signal Processing, 2008, ICSP 2008. 9th International Conference on. IEEE, 2008.
Anand, A., et al. "Automatic identification of malaria-infected RBC with digital holographic microscopy using correlation algorithms." Photonics Journal, IEEE 4.5 (2012): 1456-1464.
Ortyn, William E., et al. "Extended depth of field imaging for high speed cell analysis." Cytometry Part A 71.4 (2007): 215-231.
Sun, Yu, Stefan Duthaler, and Bradley J. Nelson. "Autofocusing algorithm selection in computer microscopy." Intelligent Robots and Systems, 2005,(IROS 2005). 2005 IEEE/RSJ International Conference on. IEEE, 2005.
Keiser, J., et al. "Acridine Orange for malaria diagnosis: its diagnostic performance, its promotion and implementation in Tanzania, and the implications for malaria control." Annals of tropical medicine and parasitology, 96.7 (2002): 643-654.
Shute, G. T., and T. M. Sodeman. "Identification of malaria parasites by fluorescence microscopy and acridine orange staining." Bulletin of the World Health Organization, 48.5 (1973): 591.
Kawamoto, Fumihiko, "Rapid diagnosis of malaria by fluorescence microscopy with light microscope and interference filter". The Lancet, vol. 337, pp. 200-202, Jan. 26, 1991.
Emma Eriksson et al: "Automated focusing of nuclei for time lapse experiments on single cells using holographic optical tweezers", Optics Express, vol. 17, No. 7 , Mar. 24, 2009, pp. 5585-5594.
Kawamoto, F. and P. F. Billingsley. "Rapid diagnosis of malaria by fluorescence microscopy." Parasitology today 8.2 (1992): 69-71.
An International Search Report and a Written Opinion both dated Jan. 15, 2016, which issued during the prosecution of Applicant's PCT/IL2015/050864.
Tek, F. Boray, Andrew G. Dempster, and Izzet Kale. "Computer vision for microscopy diagnosis of malaria." Malaria Journal 8.1 (2009): 153.
Bovik, Alan C., ed. "The essential guide to image processing", chapter 27, "Computer assisted Microscopy", pp. 777-831. Academic Press, 2009.
Thung, Ferdian, and Iping Supriana Suwardi. "Blood parasite identification using feature based recognition." Electrical Engineering and Informatics (ICEEI), 2011 International Conference on. IEEE, 2011.
Bacus, J.W., 1985. Cytometric approaches to red blood cells. Pure and Applied Chemistry, 57(4), pp. 593-598.
Centers for Disease Control and Prevention. "DPDx—Laboratory Identification of Parasitic Diseases of Public Health Concern", <http://www.cdc.gov/dpdx/diagnosticProcedures/blood/microexam. html>, Nov. 29, 2013.
An International Search Report and a Written Opinion both dated Feb. 12. 2015, which issued during the prosecution of Applicant's PCT/IL2014/050770.
U.S. Appl. No. 61/870,106, filed Aug. 26, 2013.
The use of fluorescence enhancement to improve the microscopic diagnosis of falciparum malaria Malaria Journal 2007, 6:89 http://www.malariajonmal.eom/content/6/1/89, Rebecca Guy, Paul Liu, Peter Pennefather and Ian Crandall (Jul. 6, 2007).
Leif, "Methods for Preparing Sorted Cells as Monolayer Specimens", Springer Lab Manuals, Section 7—Chapter 5, pp. 592-619, (2000).
An Office Action dated Oct. 5. 2016, which issued during the prosecution of U.S. Appl. No. 14/285,672.
Groen F C A et al: "A Comparison of Different Focus Functions for Use in Autofocus Algorithms", Cytometry, Alan Liss, New York, US, vol. 6, No. 2, Mar. 1, 1985 (Mar. 1, 1985), pp. 81-91.
Andrew Gordon et al: "Supplementary Note to Gordon et al: "Single-cell quantification of molecules . . . "". Nature Methods, Jan. 21, 2007, pp. 1-35.

Andrew Gordon et al: "Single-cell quantification of molecules and rates using open-source microscope-based cytometry", HHS Public Access Author Manuscript, vol. 4, No. 2, Jan. 21, 2007, pp. 175-181.
European Search Report dated Dec. 14, 2016. which issued during the prosecution of Applicant's European App No. 14800352.8.
An International Search Report and a Written Opinion both dated Sep. 29. 2014. which issued during the prosecution of Applicant's PCT/IL2014/050423.
An International Search Report and a Written Opinion both dated Apr. 18, 2013, which issued during the prosecution of Applicant's PCT/IL2012/050556.
An International Search Report and a Written Opinion both dated Oct. 30. 2014, which issued during the prosecution of Applicant's PCT/IL2014/050585.
Notice of Allowance dated Jan. 11. 2016, which issued during the prosecution of U.S. Appl. No. 14/440,864.
High-content live cell imaging with RNA probes: advancements in high-throughput antimalarial drug discovery BMC Cell Biology 2009, 10:45 www.biomedcentral.com/1471-2121/10/45 Serena Cervantes, Jacques Prudhomme, David Carter, Krishna G Gopi, Qian Li, Young-Tae Chang and Karine G Le Roch (Jun. 10, 2009).
Plasmodium yoelii: A differential fluorescent technique using Acridine Orange to identify infected erythrocytes and reticulocytes in Duffy knockout mouse. Experimental Parasitology vol. 110, Issue 1, May 2005, pp. 80-87. <http://www.sciencedirect.com/science/article/_pii/S001448940500038X >: Lili Xu, Asok Chaudhuri (May 31, 2005).
Notice of Allowance dated Dec. 30, 2015, which issued during the prosecution of U.S. Appl. No. 14/440,864.
Zahniser et al., Automated Slide Preparation System for the Clinical Laboratory, Cytometry, vol. 26, No. 10, pp. 30-64, (1996).
Moody, "Rapid Diagnostic Tests for Malaria Parasites", Clinical Microbiology Reviews, vol. 15, No. 1, pp. 66-78, (2002).
Knesel, "Roche Image Analysis Systems, Inc.", Acta Cytologica, vol. 40, pp. 60-66, (1996).
Life Technologies Corporation, "Counting blood cells with Countess Automated Cell Counter".pdf, four pages, (2009).
An Office Action dated Mar. 2. 2017. which issued during the prosecution of U.S. Appl. No. 14/369,251.
An International Search Report and a Written Opinion both dated Jan. 23, 2017, which issued during the prosecution of Applicant's PCT/IL2016/051025.
European Search Report dated Mar. 23, 2017. which issued during the prosecution of Applicant's European App No. 14839661.7.
An International Preliminary Report on Patentability dated Feb. 28, 2017, which issued during the prosecution of Applicant's PCT/IL2015/050864.
Roma, P. M. S., et al. "Total three-dimensional imaging of phase objects using defocusing microscopy: Application to red blood cells." Applied Physics Letters 104.25 (2014): 251107.
Agero, U., Mesquita, L.G., Neves, B.R.A., Gazzinelli, R.T. and Mesquita, O.N., 2004. Defocusing microscopy. Microscopy research and technique, 65(3), pp. 159-165.
Yazdanfar, S., Kenny, K.B., Tasimi, K., Corwin, A.D., Dixon, E.L. and Filkins, R.J., 2008. Simple and robust image-based autofocusing for digital microscopy. Optics express, 16(12), pp. 8670-8677.
Bravo-Zanoguera, M.E., Laris, C.A., Nguyen, L.K., Oliva, M. and Price, J.H., 2007. Dynamic autofocus for continuous-scanning time-delay- and-integration image acquisition in automated microscopy. Journal of biomedical optics, 12(3), pp. 034011-034011.
U.S. Appl. No. 62/042,388, filed Aug. 27, 2014.
Steven S.S. Poon, et al., "Automated Image Detection and Segmentation in Blood Smears", Cytometry, 1992, pp. 766-774, vol. 13 (9 pages total).
John F. Brenner, et al., "An Automated Microscope for Cytologic Research a Preliminary Evaluation", The Journal of Histochemistry and Cytochemistry, 1976, pp. 100-111, vol. 24, No. 1 (12 pages total).
S A H Jahanmehr, et al., "Simple Technique for Fluorescence Staining of Blood Cells with Acridine Orange", Journal of Clinical Pathology, Feb. 12, 1987, pp. 926-929 (4 pages total).

(56) References Cited

OTHER PUBLICATIONS

Anne Fohlen-Walter, PhD, et al., "Laboratory Identification of Cryoglobulinemia From Automated Blood Cell Counts, Fresh Blood Samples, and Blood Films", American Society for Clinical Pathology, Am J Clin Pathol, 2002, pp. 606-614, vol. 117 (9 pages total).

Caicai Wu, et al., "Feasibility study of the spectroscopic measurement of oxyhemoglobin using whole blood without pre-treatment", The Analyst, Mar. 1998, pp. 477-481, vol. 123 (5 pages total).

C. Briggs, et al., "Continuing developments with the automated platelet count", Blackwell Publishing Ltd, International Journal of Laboratory Hematology, Jan. 18, 2007, pp. 77-91, vol. 29 (15 pages total).

International Search Report in International Application No. PCT/IB2018/058861, dated Apr. 8, 2019.

Written Opinion in International Application No. PCT/IB2018/058861, dated Apr. 8, 2019.

Office Action dated Apr. 4, 2019, which issued during the prosecution of U.S. Appl. No. 14/914,329.

Notice of Allowance dated Mar. 20, 2019, which issued during the prosecution of U.S. Appl. No. 15/506,997.

Office Action dated Jun. 5, 2019, which issued during the prosecution of U.S. Appl. No. 15/174,490.

Office Action dated Jun. 4, 2019, which issued during the prosecution of U.S. Appl. No. 14/369,251.

Office Action dated Jun. 15, 2018 from the United States Patent and Trademark Office in copending U.S. Appl. No. 14/369,251.

Office Action dated Jun. 29, 2018 from the United States Patent and Trademark Office in copending U.S. Appl. No. 15/174,490.

Biéler, S., et al., "Improved detection of *Trypanosoma brucei* by lysis of red blood cells, concentration and LED fluorescence microscopy", Acta Tropica, vol. 121, Issue 2, 2012, pp. 135-140 (6 pages total).

Chiodini, P. L., et al., "Rapid diagnosis of malaria by fluorescence microscopy", The Lancet, vol. 337, pp. 624-625, Mar. 9, 1991 (2 pages total).

Communication dated Apr. 2, 2015, which issued during the prosecution of U.S. Appl. No. 13/338,291.

Communication dated Feb. 22, 2018, which issued during the prosecution of U.S. Appl. No. 14/369,251.

Communication dated Dec. 24, 2018 from the Intellectual Property India Patent Office in application No. 3592/MUMNP/2015.

Communication dated Jan. 28, 2019 from the United States Patent and Trademark Office in U.S. Appl. No. 15/174,490.

Communication dated Jan. 31, 2019 from the Intellectual Property India Patent Office in application No. 5069/DELNP/2012.

Communication dated Mar. 23, 2018 from the Intellectual Property India Patent Office in application 4263/DELNP/2014.

Communication dated Nov. 16, 2018 from the United States Patent and Trademark Office in U.S. Appl. No. 14/914,329.

Communication dated Sep. 25, 2015 from the United States Patent and Trademark Office in U.S. Appl. No. 13/338,291.

Communication dated Oct. 29, 2014 from the United States Patent and Trademark Office in U.S. Appl. No. 13/338,291.

Diagnostic Procedures, "Blood Specimens: Microscopic Examination", 2009, http://mcdinternational.org/trainings/malaria/english/dpdx5/HTML/Frames/DiagnosticProcedures/body_dp_bloodexamin (2 pages total).

Gallo, V., et al., "Simultaneous determination of phagocytosis of *Plasmodium falciparum*-parasitized and non-parasitized red blood cells by flow cytometry", Malaria Journal, vol. 11, No. 428, 2012, pp. 1-11 (11 pages total).

International Search Report and Written Opinion, dated Aug. 8, 2017 from the International Bureau in counterpart International application No. PCT/IL2017/050523.

International Search Report and Written Opinion, dated May 18, 2017 from the International Bureau in counterpart International application No. PCT/IL2017/050363.

International Search Report and Written Opinion, dated Aug. 30, 2017 from the International Bureau in counterpart International application No. PCT/IL2017/050526.

International Search Report and Written Opinion, dated Jul. 27, 2012 from the International Bureau in counterpart International application No. PCT/IL2011/000973.

Jager, M.M., et al., "Five-minute Giemsa stain for rapid detection of malaria parasites in blood smears", Tropical Doctor, vol. 41, Jan. 2011, pp. 33-35 (3 pages total).

Joanny, F., et. al., "In Vitro Activity of Fluorescent Dyes against Asexual Blood Stages of *Plasmodium falciparum*", Antimicrobial Agents and Chemotherapy, vol. 56, No. 11, Nov. 2012, pp. 5982-5985 (4 pages total).

Kumar, A., et al., "Enhanced Identification of Malarial Infected Objects using Otsu Algorithm from Thin Smear Digital Images", International Journal of Latest Research in Science and Technology, vol. 1, Issue 2, 2012, pp. 159-163 (5 pages total).

Le, M.-T., et al., "A novel semi-automatic image processing approach to determine *Plasmodium falciparum* parasitemia in Giemsa-stained thin blood smears", BioMed Central Cell Biology, Mar. 28, 2008, vol. 9, No. 15, pp. 1-12 (12 pages total).

Garcia, et al., "M15-A Laboratory Diagnosis of Blood-borne Parasitic Diseases; Approved Guideline", Clinical and Laboratory Standards Institute, vol. 20, No. 12, Jun. 2000 (13 pages total).

Mendiratta, DK, et al., "Evaluation of Different Methods for Diagnosis of *P. falciparum* Malaria", Indian Journal of Medical Microbiology, 2006, vol. 24, No. 1, pp. 49-51 (3 pages total).

Moon, S., et al., "An Image Analysis Algorithm for Malaria Parasite Stage Classification and Viability Quantification", PLOS ONE, vol. 8, Issue 4, Apr. 2013, pp. 1-12 (12 pages total).

Notice of Allowance dated Jan. 19, 2016, from the United States Patent and Trademark Office in U.S. Appl. No. 13/338,291.

Notice of Allowance dated Mar. 10, 2016 from the United States Patent and Trademark Office in U.S. Appl. No. 13/338,291.

Pasini, E., et. al., "A novel live-dead staining methodology to study malaria parasite viability", Malaria Journal, vol. 12, No. 190, 2013, pp. 1-10 (10 pages total).

Piruska, A., et al., "The autofluorescence of plastic materials and chips measured under laser irradiation", Lab on a Chip, vol. 5, 2005, pp. 1348-1354 (7 pages total).

Sheikh, H., et al., "Blood Cell Identification Using Neural Networks", Proceedings of the IEEE 2nd Annual Northeast Bioengineering Conference, Mar. 1996, pp. 119-120 (2 pages total).

Tek, F. et al., "Parasite detection and identification for automated thin blood film malaria diagnosis", Computer Vision and Image Understanding, vol. 114, Issue 1, 2010, pp. 21-32 (12 pages total).

Unitaid, "Malaria Diagnostics Technology and Market Landscape", 2nd Edition, Jul. 2014, pp. 1-140 (148 pages total).

Wissing, et al., "Illumination of the Malaria Parasite *Plasmodium falciparum* Alters Intracellular pH", The Journal of Biological Chemistry, vol. 277, No. 40, Issue of Oct. 4, pp. 37747-37755, 2002, (10 pages total).

Wright, J., "A Rapid Method for the Differential Staining of Blood Films and Malarial Parasites", Journal of Medical Research, vol. 7, No. 1, 1902, pp. 138-144 (7 pages total).

Yao, LN., et al., "Pathogen Identification and Clinical Diagnosis for One Case Infected with *Babesia*", Chinese Journal of Parasitology Parasitic Diseases, vol. 30, No. 2, Apr. 2012, pp. 118-121 (4 pages total).

METHODS AND APPARATUS FOR DETECTING AN ENTITY IN A BODILY SAMPLE

CROSS-REFERENCE TO RELATED APPLICATIONS

The present application is a US national phase application of PCT Application No. PCT/IL/2016/051025 to Eshel (published as WO 17/046799), filed Sep. 15, 2016, which claims priority from U.S. Provisional Patent Application No. 62/219,889 to Eshel, filed Sep. 17, 2015, entitled "Methods of detecting a pathogen in a bodily sample and system thereof."

U.S. Provisional Patent Application No. 62/219,889 to Eshel is incorporated herein by reference.

FIELD OF EMBODIMENTS OF THE INVENTION

Some applications of the presently disclosed subject matter relate generally to detecting entities in a bodily sample, and in particular, to detecting pathogens automatically using image processing and classification.

BACKGROUND

The primary method of detection of certain pathogenic infections within a bodily sample (e.g., a blood sample) is the microscopic examination of the bodily sample, and visual confirmation of the presence and concentration of the pathogen. Staining a bodily sample with a stain or dye prior to microscopic examination is often used to enhance contrast in the microscopic image, and to visually highlight cells having a particular biological makeup. In particular, some fluorescent dyes have an affinity for nucleic acid in cells. When excited by fluorescent light at an appropriate wavelength, the nucleic acid will fluoresce. Accordingly, fluorescent dyes are sometimes used to differentially stain parts of a cell for detection under a microscope. For example, when excited by blue light, the fluorochrome Acridine Orange bound to DNA will emit green light, and when bound to RNA will emit red light. Blood pathogens such as Anaplasma marginale, Hemobartonella, trypanosomes, *Plasmodium* spp., *Babesia* spp. and others have all been detected with Acridine Orange.

While the primary method of detecting pathogens remains visual identification in a microscopic bright field image, fluorescent microscopy has been used as well, though to a lesser extent. However, in both cases, detection of a pathogenic infection by manual identification of pathogens suffers from two main drawbacks: many settings (especially rural) are not equipped to perform the test, and the accuracy of the results depends on both the skill of the person examining the sample and the levels of the pathogen in the sample. Accordingly, attempts have been made to automate the detection of pathogens in a bodily sample.

SUMMARY OF EMBODIMENTS

In accordance with some applications of the present invention, one or more microscope images of a bodily sample (e.g., a blood sample) are acquired, using a microscope of a microscope system. A computer processor identifies at least one element as being a pathogen candidate (i.e., a constituent element within the sample that exhibits characteristics that indicate that it may be a pathogen, and is therefore a candidate for being a pathogen) within the images. For example, the images may be images of a blood sample that were acquired while the sample was stained with a stain or dye that is configured to stain DNA and/or RNA within the sample, and the computer processor may identify the candidate by detecting stained elements (e.g., fluorescing elements) within the images. The computer processor extracts, from the one or more images, at least one candidate-informative feature associated with the pathogen candidate, and at least one sample-informative feature that is indicative of contextual information related to the bodily sample. The likelihood of the bodily sample being infected with a pathogenic infection is classified by processing the candidate-informative feature in combination with the sample-informative feature. An output is typically generated on an output device in response to the classification.

For some applications, in response to the candidate-informative feature, the computer processor performs a first classifying, in which a likelihood of the pathogen candidate being a pathogen is classified. In response to the first classifying in combination with the sample-informative feature, the computer processor a second classifying in which a likelihood of the bodily sample containing a pathogenic infection is classified. For some applications, the first classifying (in which a likelihood of the pathogen candidate being a pathogen is classified) is performed in response to the candidate-informative feature in combination with the sample-informative feature. For some applications, the computer processor classifies a pathogenic infection in the bodily sample as a given type of pathogenic infection (e.g., *Plasmodium*, a given strain of *Plasmodium*, and/or *Plasmodium* of a given age or age range), by processing the candidate-informative feature in combination with the sample-informative feature.

For some applications, the candidate-informative feature includes a size of the pathogen candidate (e.g. dimension, length, circumference, minimum width, maximum width, area, and/or relative size of the candidate with respect to other candidates or entities), a shape of the pathogen candidate, a motion of the pathogen candidate, an intensity of the pathogen candidate, a location of the pathogen candidate within the bodily sample (including proximity, abutment, and/or overlap of the candidate with respect to other candidates or entities), a property of a cell overlapping the pathogen candidate, a color of the pathogen candidate (including intensity and pattern of staining), a texture (e.g., contour) of the pathogen candidate, and/or a sharpness of a boundary of the pathogen candidate. Further non-limiting examples of candidate-informative features are described for example in US 2012/0169863 to Bachelet, and/or US 2015/0037806 to Pollak, both of which applications are incorporated herein by reference.

For some applications, sample-informative features include a size of one or more non-pathogen-candidate constituents in the bodily sample, a shape of one or more non-pathogen-candidate constituents within the bodily sample, an intensity of one or more non-pathogen-candidate constituents within the bodily sample, a quantity of cells of a given cell type within the bodily sample, a distribution of cells of a given cell type within the bodily sample, and/or a distribution of pathogen candidates within the bodily sample.

There is therefore provided, in accordance with some applications of the present invention, apparatus including:

a microscope system configured to acquire one or more microscope images of a bodily sample;

an output device; and at least one computer processor configured to:
  identify, in the one or more images, at least one element as being a pathogen candidate,
  extract, from the one or more images, at least one candidate-informative feature associated with the pathogen candidate,
  extract, from the one or more images, at least one sample-informative feature that is indicative of contextual information related to the bodily sample;
  classifying a likelihood of the bodily sample being infected with a pathogenic infection, by processing the candidate-informative feature in combination with the sample-informative feature, and
  generate an output upon the output device, in response thereto.

In some applications:
  the microscope system is configured to acquire one or more microscope images of a bodily sample that is stained with a stain; and
  the at least one computer processor is configured to identify at least one element as being a pathogen candidate by identifying the at least one element as being a pathogen candidate by identifying that the at least one element is stained.

In some applications, the at least one computer processor is configured to process the candidate-informative feature in combination with the sample-informative feature by:
  in response to the candidate-informative feature, performing a first classifying, in which a likelihood of the pathogen candidate being a pathogen is classified, and
  in response to the first classifying in combination with the sample-informative feature, performing a second classifying in which a likelihood of the bodily sample containing a pathogenic infection is classified.

In some applications, the at least one computer processor is configured to process the candidate-informative feature in combination with the sample-informative feature by:
  in response to the candidate-informative feature in combination with the sample-informative feature, performing a first classifying, in which a likelihood of the pathogen candidate being a pathogen is classified, and
  at least partially in response to the first classifying, performing a second classifying in which in which a likelihood of the bodily sample containing a pathogenic infection is classified.

In some applications, the at least one computer processor is configured to extract, from the one or more images, at least one candidate-informative feature associated with the pathogen candidate by extracting, from the one or more images, at least one candidate-informative feature associated with the pathogen candidate, the candidate-informative feature being a feature selected from the group consisting of: a size of the pathogen candidate, a shape of the pathogen candidate, a motion of the pathogen candidate, an intensity of the pathogen candidate, a location of the pathogen candidate within the bodily sample, a property of a cell overlapping the pathogen candidate, a color of the pathogen candidate, a texture of the pathogen candidate, and a sharpness of a boundary of the pathogen candidate.

In some applications, the at least one computer processor is configured to extract, from the one or more images, at least one sample-informative feature that is indicative of contextual information related to the bodily sample by extracting, from the one or more images, at least one sample-informative feature selected from the group consisting of: a size of one or more non-pathogen-candidate constituents in the bodily sample, a shape of one or more non-pathogen-candidate constituents within the bodily sample, an intensity of one or more non-pathogen-candidate constituents within the bodily sample, a quantity of cells of a given cell type within the bodily sample, a distribution of cells of a given cell type within the bodily sample, and a distribution of pathogen candidates within the bodily sample.

In some applications:
  the microscope system is configured to acquire the one or more microscope images of the bodily sample by acquiring one or more microscope images of a bodily sample that is stained with a stain; and
  the at least one computer processor is configured to extract, from the one or more images, at least one sample-informative feature that is indicative of contextual information related to the bodily sample by extracting, from the one or more images, at least one sample-informative feature that is indicative of a quality of staining of the bodily sample by the stain.

In some applications, the at least one computer processor is configured to extract, from the one or more images, at least one sample-informative feature that is indicative of contextual information related to the bodily sample by extracting, from the one or more images, at least one sample-informative feature that is indicative of a foreign object that is present in the bodily sample.

In some applications, the bodily sample includes a bodily sample selected from the group consisting of: a blood sample, a diluted blood sample, a sample including predominantly red blood cells, and a diluted sample including predominantly red blood cells, and the microscope system is configured to acquire one or more images of the selected bodily sample.

In some applications, the at least one computer processor is configured to extract, from the one or more images, at least one sample-informative feature that is indicative of contextual information related to the bodily sample by extracting, from the one or more images, a size of one or more red blood cells that are present within the bodily sample.

In some applications, the at least one computer processor is configured to extract, from the one or more images, at least one sample-informative feature that is indicative of contextual information related to the bodily sample by extracting, from the one or more images, an indication of a presence of Howell Jolly bodies within the bodily sample.

In some applications, the at least one computer processor is configured to extract, from the one or more images, at least one sample-informative feature that is indicative of contextual information related to the bodily sample by extracting, from the one or more images, a concentration of platelets within the bodily sample.

In some applications, the at least one computer processor is configured to extract, from the one or more images, at least one sample-informative feature that is indicative of contextual information related to the bodily sample by extracting, from the one or more images, a relationship between a number of reticulocytes associated with candidates and a number of mature red blood cells associated with candidates.

In some applications, the at least one computer processor is configured to extract, from the one or more images, at least one sample-informative feature that is indicative of contextual information related to the bodily sample by extracting, from the one or more images, a concentration of reticulocyte bodies within the bodily sample.

In some applications, the at least one computer processor is configured to classify the likelihood of the bodily sample being infected with the pathogenic infection by adjusting a threshold for a positive determination of a pathogenic infection, based upon the concentration of the reticulocyte bodies within the bodily sample.

In some applications, the at least one computer processor is configured to classify a pathogenic infection in the bodily sample as containing one or more given types of pathogen, by processing the candidate-informative feature in combination with the sample-informative feature.

In some applications, the at least one computer processor is configured to classify the pathogenic infection in the bodily sample as containing one or more given types of pathogen by classifying the pathogenic infection as containing one or more categories of pathogen selected from the group consisting of: *Plasmodium*, a given strain of *Plasmodium*, *Plasmodium* of a given age, and *Plasmodium* of a given age range.

In some applications:

the bodily sample includes a bodily sample selected from the group consisting of: a blood sample, a diluted blood sample, a sample comprising predominantly red blood cells, and a diluted sample comprising predominantly red blood cells;

the at least one computer processor is configured to extract, from the one or more images, at least one sample-informative feature that is indicative of contextual information related to the bodily sample by extracting, from the one or more images, a relationship between a number of reticulocytes associated with candidates and a number of mature red blood cells associated with candidates; and the at least one computer processor is configured to classify the pathogenic infection in the bodily sample as containing one or more given types of pathogen by classifying the pathogenic infection in the bodily sample as containing the given type of pathogen, at least partially based upon the relationship between a number of reticulocytes associated with candidates and a number of mature red blood cells associated with candidates.

In some applications:

the bodily sample includes a bodily sample selected from the group consisting of: a blood sample, a diluted blood sample, a sample comprising predominantly red blood cells, and a diluted sample comprising predominantly red blood cells;

the at least one computer processor is configured to extract, from the one or more images, at least one sample-informative feature that is indicative of contextual information related to the bodily sample by extracting, from the one or more images, shapes of red blood cells within the bodily sample, and the at least one computer processor is configured to classify the pathogenic infection in the bodily sample as containing the given type of pathogen by classifying the pathogenic infection in the bodily sample as the given type of pathogenic infection, at least partially based upon the shapes of the red blood cells within the bodily sample.

In some applications:

the bodily sample includes a bodily sample selected from the group consisting of: a blood sample, a diluted blood sample, a sample comprising predominantly red blood cells, and a diluted sample comprising predominantly red blood cells;

the at least one computer processor is configured to extract, from the one or more images, at least one sample-informative feature that is indicative of contextual information related to the bodily sample by extracting, from the one or more images, sizes of red blood cells within the bodily sample, and the at least one computer processor is configured to classify the pathogenic infection in the bodily sample as containing the given type of pathogen by classifying the pathogenic infection in the bodily sample as the given type of pathogenic infection, at least partially based upon the sizes of the red blood cells within the bodily sample.

There is further provided, in accordance with some applications of the present invention, a method including:

acquiring one or more microscope images of a bodily sample, using a microscope;

using at least one computer processor:

in the one or more images, identifying at least one element as being a pathogen candidate;

extracting, from the one or more images, at least one candidate-informative feature associated with the pathogen candidate;

extracting, from the one or more images, at least one sample-informative feature that is indicative of contextual information related to the bodily sample;

classifying a likelihood of the bodily sample being infected with a pathogenic infection, by processing the candidate-informative feature in combination with the sample-informative feature; and generating an output, in response thereto.

There is further provided, in accordance with some applications of the present invention, a computer software product, for use with a bodily sample, an output device, and a microscope system configured to acquire one or more microscope images of a bodily sample, the computer software product including a non-transitory computer-readable medium in which program instructions are stored, which instructions, when read by a computer cause the computer to perform the steps of: in the one or more images, identifying at least one element as being a pathogen candidate; extracting, from the one or more images, at least one candidate-informative feature associated with the pathogen candidate; extracting, from the one or more images, at least one sample-informative feature that is indicative of contextual information related to the bodily sample; classifying a likelihood of the bodily sample being infected with a pathogenic infection, by processing the candidate-informative feature in combination with the sample-informative feature; and generating an output upon the output device, in response thereto.

There is further provided, in accordance with some applications of the present invention, apparatus including:

a microscope system configured to acquire one or more microscope images of a bodily sample;

an output device; and at least one computer processor configured to:

extract, from the one or more images, at least one sample-informative feature that is indicative of contextual information related to the bodily sample, at least partially based upon the extracted sample-informative feature:

identify that there is a defect associated with the bodily sample disposed in the sample carrier, and classify a source of the defect, and response thereto, generate an output on the output device that is indicative of the source of the defect.

In some applications, the at least one computer processor is configured to classify the source of the defect by classifying the source as being at least one source selected from the group consisting of: the sample carrier, a given portion of the sample carrier, the bodily sample, and a diluent in which the sample has been diluted.

There is further provided, in accordance with some applications of the present invention, a method including:
acquiring one or more microscope images of a bodily sample disposed in a sample carrier, using a microscope;
using at least one computer processor:
extracting, from the one or more images, at least one sample-informative feature that is indicative of contextual information related to the bodily sample;
at least partially based upon the extracted sample-informative feature:
identifying that there is a defect associated with the bodily sample disposed in the sample carrier, and classifying a source of the defect; and
in response thereto, generating an output that is indicative of the source of the defect.

There is further provided, in accordance with some applications of the present invention, a computer software product, for use with a bodily sample, an output device and a microscope system configured to acquire one or more microscope images of a bodily sample, the computer software product including a non-transitory computer-readable medium in which program instructions are stored, which instructions, when read by a computer cause the computer to perform the steps of: extracting, from the one or more images, at least one sample-informative feature that is indicative of contextual information related to the bodily sample; at least partially based upon the extracted sample-informative feature: identifying that there is a defect associated with the bodily sample disposed in the sample carrier, and classifying a source of the defect; and in response thereto, generating an output on the output device that is indicative of the source of the defect.

There is further provided, in accordance with some applications of the present invention, apparatus for classifying a bodily sample, the apparatus including:
a microscope system configured to acquire one or more microscope images of the bodily sample;
an output device; and
at least one computer processor configured to:
identify, in the one or more images, at least one element as being a candidate of a given entity,
extract, from the one or more images, at least one candidate-informative feature associated with the identified element,
extract, from the one or more images, at least one sample-informative feature that is indicative of contextual information related to the bodily sample,
process the candidate-informative feature in combination with the sample-informative feature, and
generate an output upon the output device, in response thereto.

In some applications, the bodily sample includes a sample that contains blood, and the computer processor is configured to identify at least one element as being a candidate of a given entity by identifying at least one element as being a candidate of a given entity within the blood.

In some applications, the computer processor is configured to identify at least one element as being a candidate of a given entity by identifying at least one element as being a pathogen candidate.

There is further provided, in accordance with some applications of the present invention, a method for classifying a bodily sample, the method including:
acquiring one or more microscope images of the bodily sample, using a microscope;
using at least one computer processor:
in the one or more images, identifying at least one element as being a candidate of a given entity;
extracting, from the one or more images, at least one candidate-informative feature associated with the identified element;
extracting, from the one or more images, at least one sample-informative feature that is indicative of contextual information related to the bodily sample;
processing the candidate-informative feature in combination with the sample-informative feature; and
generating an output, in response thereto.

In some applications, the bodily sample includes a sample that contains blood, and identifying at least one element as being a candidate of a given entity includes identifying at least one element as being a candidate of a given entity within the blood.

In some applications, identifying at least one element as being a candidate of a given entity includes identifying at least one element as being a pathogen candidate.

There is further provided, in accordance with some applications of the present invention, a computer software product, for use with a bodily sample, an output device and a microscope system configured to acquire one or more microscope images of a bodily sample, the computer software product including a non-transitory computer-readable medium in which program instructions are stored, which instructions, when read by a computer cause the computer to perform the steps of: in the one or more images, identifying at least one element as being a candidate of a given entity; extracting, from the one or more images, at least one candidate-informative feature associated with the identified element; extracting, from the one or more images, at least one sample-informative feature that is indicative of contextual information related to the bodily sample; processing the candidate-informative feature in combination with the sample-informative feature; and generating an output on the output device, in response thereto.

There is further provided, in accordance with some applications of the present invention, apparatus including:
a microscope system configured to acquire one or more microscope images of a bodily sample;
an output device; and
at least one computer processor configured to:
in the one or more images, identify at least one element as being a candidate of a given entity,
extract, from the one or more images, at least one candidate-informative feature associated with the candidate,
extract, from the one or more images, at least one sample-informative feature that is indicative of contextual information related to the bodily sample,
process the candidate-informative feature in combination with the sample-informative feature, and
in response thereto, perform an action selected from the group consisting of: generating an output on the output device indicating that presence of an infection within the bodily sample could not be determined with a sufficient degree of reliability, generating an output on the output device indicating that a portion of the sample should be re-imaged, generating an output on the output device indicating that a portion of the sample should be re-imaged using different settings, driving the microscope system to re-image a portion of the sample, driving the microscope system to re-image a portion of the sample using different settings, and modulating a frame rate at which microscope images are acquired by the microscope system.

There is further provided, in accordance with some applications of the present invention, a method including:
acquiring one or more microscope images of a bodily sample, using a microscope;
using at least one computer processor:
in the one or more images, identifying at least one element as being a candidate of a given entity;
extracting, from the one or more images, at least one candidate-informative feature associated with the candidate;
extracting, from the one or more images, at least one sample-informative feature that is indicative of contextual information related to the bodily sample;
processing the candidate-informative feature in combination with the sample-informative feature; and
in response thereto, performing an action selected from the group consisting of: generating an output indicating that presence of an infection within the bodily sample could not be determined with a sufficient degree of reliability, generating an output indicating that a portion of the sample should be re-imaged, generating an output indicating that a portion of the sample should be re-imaged using different settings, driving the microscope to re-image a portion of the sample, driving the microscope to re-image a portion of the sample using different settings, and modulating a frame rate at which microscope images are acquired by the microscope.

There is further provided, in accordance with some applications of the present invention, a computer software product, for use with a bodily sample, an output device and a microscope system configured to acquire one or more microscope images of a bodily sample, the computer software product including a non-transitory computer-readable medium in which program instructions are stored, which instructions, when read by a computer cause the computer to perform the steps of: in the one or more images, identifying at least one element as being a candidate of a given entity; extracting, from the one or more images, at least one candidate-informative feature associated with the candidate; extracting, from the one or more images, at least one sample-informative feature that is indicative of contextual information related to the bodily sample; processing the candidate-informative feature in combination with the sample-informative feature; and in response thereto, performing an action selected from the group consisting of: generating an output on the output device indicating that presence of an infection within the bodily sample could not be determined with a sufficient degree of reliability, generating an output on the output device indicating that a portion of the sample should be re-imaged, generating an output on the output device indicating that a portion of the sample should be re-imaged using different settings, driving the microscope system to re-image a portion of the sample, driving the microscope system to re-image a portion of the sample using different settings, and modulating a frame rate at which microscope images are acquired by the microscope system.

There is further provided, in accordance with some applications of the present invention, apparatus including:
a microscope system configured to acquire one or more microscope images of a bodily sample;
an output device; and
at least one computer processor configured to:
identify within one or more images of the set of images elements as being candidates of one or more given entities,
extract, from the one or more images, candidate-informative features associated with the candidates,
extract, from the candidate-informative features, two or more sample-informative features related to the bodily sample,
determine a characteristic of the bodily sample, by processing the two or more sample-informative features, and
generate an output, in response thereto.

In some applications, the bodily sample includes a bodily sample that contains blood, and the computer processor is configured to extract the candidate-informative features associated with the candidates by extracting one or more candidate-informative features associated with a pathogen candidate within the blood, and extracting one or more candidate informative features associated with platelets within the blood.

In some applications, the bodily sample includes a bodily sample that contains blood, and the computer processor is configured to extract the candidate-informative features associated with the candidates by extracting one or more candidate-informative features associated with a pathogen candidate within the blood, and extracting one or more candidate informative features associated with reticulocytes within the blood.

In some applications:
the bodily sample includes a bodily sample that contains blood,
the computer processor is configured to identify within one or more images of the set of images elements as being candidates of one or more given entities by identifying elements as being pathogen candidates, and
the computer processor is configured to extract, from the candidate-informative features, two or more sample-informative features related to the bodily sample by extracting, from the candidate-informative features, two or more sample-informative features selected from the group consisting of: number of pathogen candidates in the sample, type of pathogen candidates in the sample, brightness of the candidates relative to background brightness, a probability of candidates being pathogens, number of candidates that have a probability of being a pathogen that exceeds a threshold, number of candidates that have a probability of being a given type of pathogen that exceeds a threshold, a number of platelets in the sample, brightness of platelets, a number of reticulocytes in the sample, a number of reticulocytes infected by pathogens in the sample, a proximity of the candidates to red blood cells, and a number of red blood cells in the sample.

There is further provided, in accordance with some applications of the present invention, a method for classifying a bodily sample, the method including:
acquiring a set of microscope images of the bodily sample, using a microscope;
using at least one computer processor:
identifying within one or more images of the set of images elements as being candidates of one or more given entities;
extracting, from the one or more images, candidate-informative features associated with the candidates;
extracting, from the candidate-informative features, two or more sample-informative features related to the bodily sample;
determining a characteristic of the bodily sample, by processing the two or more sample-informative features; and
generating an output, in response thereto.

There is further provided, in accordance with some applications of the present invention, a computer software product, for use with a bodily sample, an output device and a microscope system configured to acquire one or more microscope images of a bodily sample, the computer software product including a non-transitory computer-readable medium in which program instructions are stored, which instructions, when read by a computer cause the computer to perform the steps of: identifying within one or more images of the set of images elements as being candidates of one or more given entities; extracting, from the one or more images, candidate-informative features associated with the candidates; extracting, from the candidate-informative features, two or more sample-informative features related to the bodily sample; determining a characteristic of the bodily sample, by processing the two or more sample-informative features; and generating an output on the output device, in response thereto.

The present invention will be more fully understood from the following detailed description of embodiments thereof, taken together with the drawings, in which:

DETAILED DESCRIPTION OF EMBODIMENTS

Figure 1:
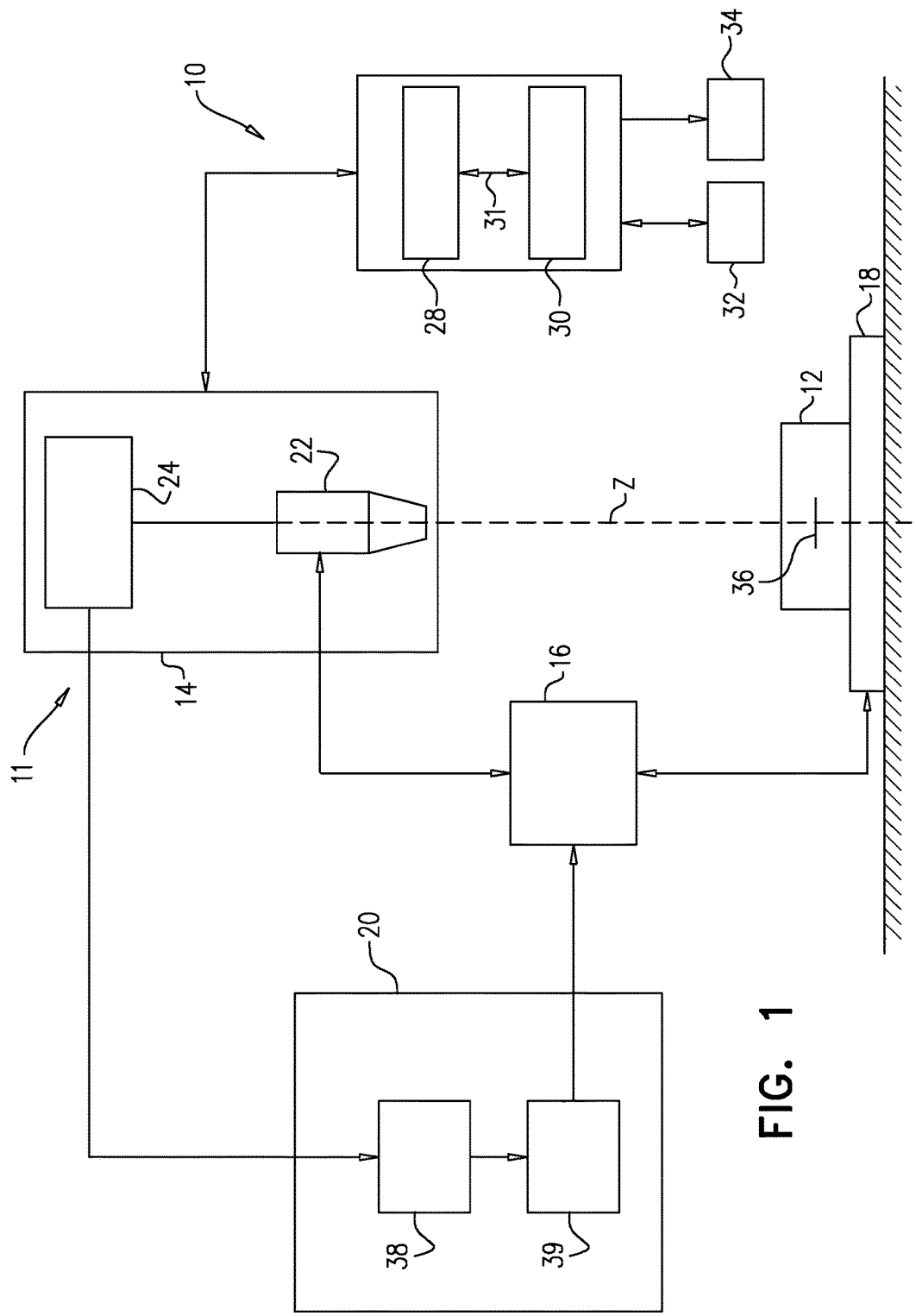
FIG. 1 is a generalized functional diagram of a pathogen detection system, in accordance some applications of the present invention.

Reference is now made to FIG. 1, which is a functional diagram of a pathogen detection system 10, in accordance with some applications of the present invention. Pathogen detection system 10 includes a processor 28 operatively coupled to a memory 30, e.g. by a communication bus 31. In certain embodiments, pathogen detection system 100 can optionally include or be operatively coupled to a microscope system 11. Microscope system 11 is typically a digital microscope that includes an imaging module 14, a focus variation module 16, a sample carrier 18 and an autofocus system 20. For some applications, microscope system 11 is generally similar to the microscope system described in US 2014/0347459 to Greenfield, which is incorporated herein by reference.

Typically, imaging module 14 includes an optical unit 22 and an image sensor unit 24. Optical unit 22 is configured to form a magnified image of a bodily sample 12 (for example, a blood sample) by conjugating a focus plane 36 and an image plane. The image sensor unit 24 typically includes an image sensor, for example a charge-coupled-device (CCD), complementary metal-oxide-semiconductor (CMOS) sensor, and/or a matrix sensor, positioned in the image plane of the optical unit 22 so as to sense the magnified image.

Computer processor 28 typically receives and processes images. The computer processor communicates with memory 30, and images are received by the processor via the memory. Via a user interface 32, a user (e.g., a laboratory technician) sends instructions to the computer processor. For some applications, the user interface includes a keyboard, a mouse, a joystick, a touchscreen device (such as a smartphone or a tablet computer), a touchpad, a trackball, a voice-command interface, and/or other types of user interfaces that are known in the art. Typically, the computer processor generates an output via an output device 34. Further typically, the output device includes a display, such as a monitor, and the output includes an output that is displayed on the display. For some applications, the processor generates an output on a different type of visual, text, graphics, tactile, audio, and/or video output device, e.g., speakers, headphones, a smartphone, or a tablet computer. For some applications, user interface 32 acts as both an input interface and an output interface, i.e., it acts as an input/output interface. For some applications, the processor generates an output on a computer-readable medium (e.g., a non-transitory computer-readable medium), such as a disk, or a portable USB drive, and/or generates an output on a printer.

Microscope system 11 can, in certain embodiments, include a local processor that controls at least some of the processes of microscope system 11, for example, image acquisition and/or communication with other components, including other components of pathogen detection system 10 and components external to pathogen detection system 10. In certain other embodiments, processor 28 can control one or more processes of microscope system 11 including, e.g. image acquisition and/or communication. Optionally, pathogen detection system 10 can include or be operatively coupled to a plurality of digital microscopes. Optionally, each respective digital microscope in the plurality of digital microscopes has its own local processor.

In certain embodiments, memory 30 can be configured to store imaging information, program data and/or executable program instructions for detecting a pathogen in a bodily sample, as will be detailed below with reference to FIG. 2. Memory 30 can be, e.g., volatile memory or non-volatile memory. In certain embodiments, memory 30 is non-volatile memory, e.g. hard disk drive, flash memory, etc.

For some applications, microscope system 11 is configured to capture one or more high magnification digital images of a bodily sample. Optionally, the one or more digital images include images that cover different portions of the bodily sample. Optionally, the images do not overlap (or overlap by less than 5 percent or less than 1 percent). Optionally, the images include images that overlap and are taken at different depths of focus, and/or with different lighting conditions. Optionally, the one or more digital images include sets of images that do not overlap (or overlap by less than 5 percent or less than 1 percent), but each of the sets includes images of another set, taken with different lighting conditions. In certain embodiments, microscope system 11 is configured to capture images under a plurality of lighting conditions, including, e.g., bright field, blue light, and ultraviolet light, as will be further detailed below.

In accordance with some applications, bodily sample 12 (e.g., a blood sample) is scanned by the microscope system, such that a plurality of portions of the bodily sample are imaged. For some applications, a plurality of images are acquired of one or more portions of the bodily sample, with each of the plurality of images being acquired under respective imaging conditions. For example, two images of a portion of the bodily sample may be acquired using, respectively, imaging conditions that allow detection of cells (e.g., bright-field) and imaging conditions that allow visualization of stained bodies (e.g. appropriate fluorescent illumination).

Image sensor unit 24 may output acquired digital images to output device 34 (which may include a display) and/or to the autofocus system 20. Focus variation module 16 may be configured to vary a distance between the focus plane 36 of the optical unit 22 and the sample carrier 18. Focus variation module 16 may be operated manually or automatically via a mechanical interface which may, for example, modify the position of the sample carrier 18 along an optical axis Z of the optical unit 22. Alternatively or additionally, focus variation module 16 may be commanded by autofocus system 20. For example, the focus variation module 16 may vary the distance between the sample carrier 18 and the focus plane by (1) modifying the position of optical unit 22 along the optical axis Z, (2) modifying the position of the sample carrier 18 along the position of the optical axis Z (e.g., by moving a stage upon which the sample carrier is placed), (3) modifying the position of the focus plane by, for example, changing a focal length of the optical unit 22, or a combination thereof.

The sample carrier 18 may comprise a plate. Sample carrier 18 may be configured to accommodate bodily sample 12. The carrier may be any carrier known in the art for holding a biological sample. Optionally, the bottom surface of the carrier is essentially flat, to allow cells in contact therewith to be at about the same distance from the focal plane of the microscope. Examples include carrier slides, laboratory receptacles, dishes, plates, multi-well plates, test tubes (e.g. with a flat bottom), microfluidic cells, cartridges, and the like.

Autofocus system 20 may comprise an autofocus computation module 38 and an autofocus adaption module 39. The autofocus computation module may be connected to the image sensor unit 24 so as to receive images acquired by the imaging module 14. The autofocus adaptation module may be connected to the focus variation module 16 and may be configured to command the focus variation module 16, e.g., as described above.

For some applications, processor 28 includes one or more functional modules, such as a feature extraction module, a candidate classifier, a sample classifier, and a diagnostics module. For some applications, processor 28 is configured to process imaging information by extracting features contained within the imaging information. Typically, the processor is configured to extract at least one sample-informative feature and at least one candidate-informative feature. For some applications, the processor is further configured to process the at least one sample-informative feature to obtain contextual information, and to process the at least one candidate-informative feature to obtain candidate data, as will be further detailed below.

Typically, the processor is configured to classify a likelihood of a candidate (i.e., a constituent element within the sample that exhibits characteristics that indicate that it may be a pathogen, and is therefore a candidate for being a pathogen) being a pathogen at least partially based upon the at least one candidate-informative feature. Further typically, the processor is configured to classify a likelihood of the bodily sample being infected with a pathogenic infection, by processing the at least one candidate-informative feature in combination with the at least one sample-informative feature.

For some applications, the processor is programmed to classify the likelihood of a candidate being a pathogen, and/or to classify a likelihood of sample being infected with a pathogenic infection using classification and/or machine learning algorithms, e.g. support vector machines, neural networks, naive Bayes algorithms, etc. Additional examples of types of classification and/or machine learning algorithms which can be used by the processor are described in US 2012/0169863 to Bachelet and/or US 2015/0037806 to Pollak, both of which applications are incorporated herein by reference. For some applications, the computer processor is trained, in advance of being used to analyze a bodily sample, using training images of bodily samples.

For some applications, if a bodily sample is determined to be infected with a pathogenic infection (or if it is determined that the likelihood of the bodily sample being infected with a pathogenic infection exceeds a threshold), the computer processor is further configured to extract diagnostic information about the pathogenic infection in accordance with at least the at least one sample-informative feature.

It is noted that the teachings of the presently disclosed subject matter are not bound by the specific pathogen detection system described with reference to FIG. 1. Equivalent and/or modified functionality can be consolidated or divided in another manner and can be implemented in any appropriate combination of software, firmware and hardware. The processor can be implemented as a suitably programmed computer.

Figure 2:
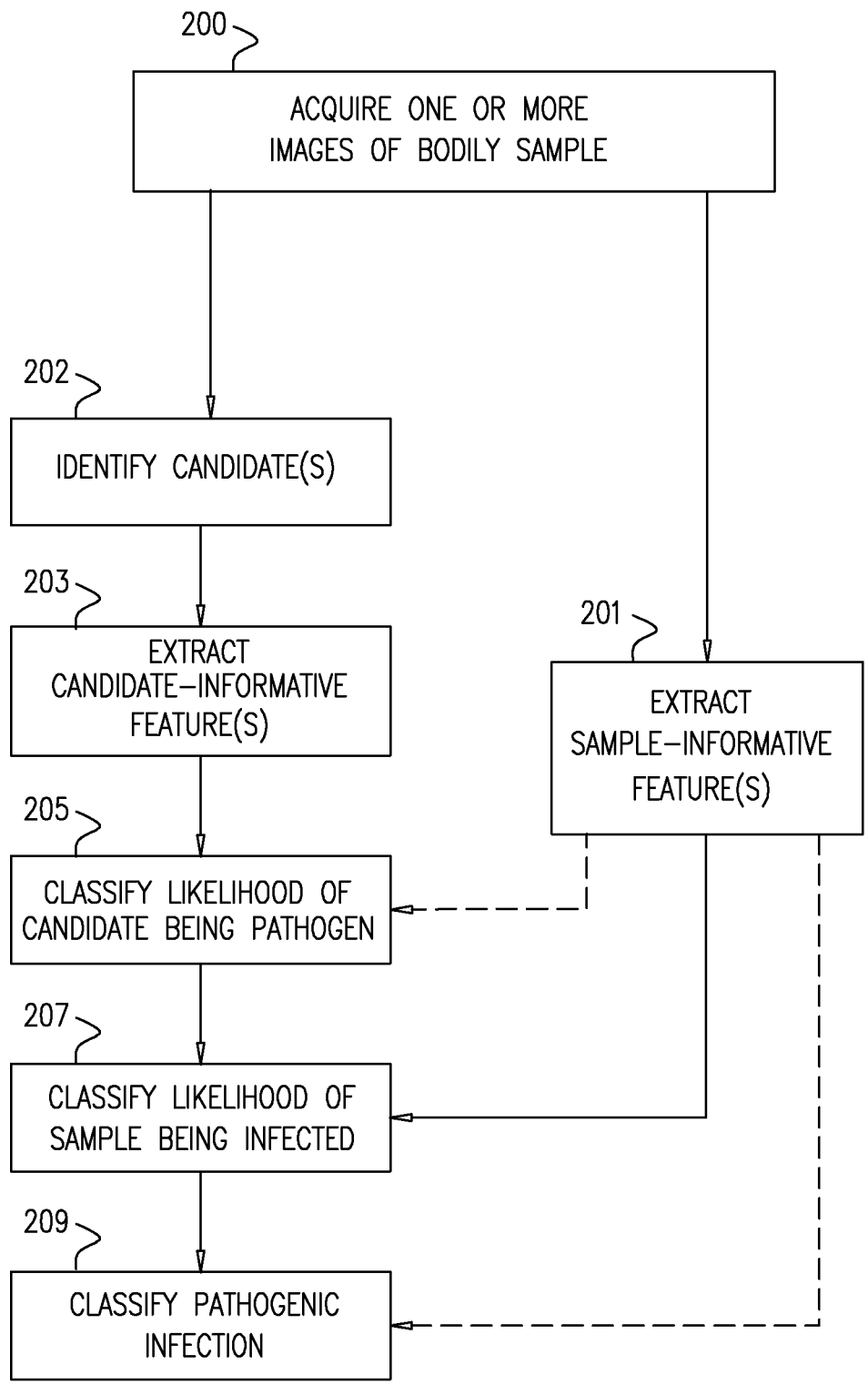
FIG. 2 is a generalized flow chart of steps that are performed, in accordance with some applications of the present invention.

Reference is now made to FIG. 2, which shows a generalized flow chart of a method for detecting a pathogenic infection in a bodily sample (e.g., a blood sample), in accordance with some applications of the present invention.

In a first step 200, one or more images of the bodily sample are acquired by microscope system 11. The one or more images, data informative of one or more images, or data derived from one or more images (collectively referred to herein as "imaging information") are typically stored in memory 30. The imaging information is then analyzed by processor 28, as described in further detail hereinbelow. It is noted that in the present application, the computer processor is described as extracting features from the one or more images. This terminology should be interpreted as including extracting the features from data informative of the one or more images, or data derived from the one or more images, and should not be interpreted as being limited to directly extracting the features from the one or more images themselves.

For some applications, the imaging information is informative of at least one high magnification microscopic view of the sample. Alternatively or additionally, the imaging information is informative of a plurality of images, including, e.g., images of different portions of the sample, images of the same portion of the sample taken at different focal depths, and/or different lighting conditions, and/or at different times.

The bodily sample may be from any living creature but preferably from warm blooded animals. Typically, the bodily sample is a blood sample. The sample can be any blood sample or a portion thereof comprising one or more red blood cells. Optionally, the sample comprises predominantly red blood cells (i.e., a majority of the cells (e.g., at least 60 percent of the cells) in the sample are red blood cells). Optionally, the sample also comprises at least one of platelets and white blood cells. Optionally, the blood sample is diluted. Optionally, the dilution is performed or the sample is otherwise prepared such that the concentration of cells on the surface that is imaged is between 3,000 and 30,000 cells (e.g., red blood cells) per square mm. Optionally, the blood sample is diluted with a staining solution.

Optionally, the sample or staining solution comprises one or more suitable dyes or stains (optionally, comprising one or more fluorescent dyes). In some embodiments, the blood sample is selected from whole blood sample, red blood cell sample, buffy coat sample, plasma sample, serum sample, a sample from any other blood fraction, or any combination thereof.

Optionally, the sample forms a monolayer on the surface of sample carrier 18. In the context of the present disclosure, when referring to a monolayer of cells, it is to be understood as encompassing the distribution of cells on a surface as an essentially single layer, where at least 50 percent (at times, at least 60 percent, 70 percent, 80 percent or even 90 percent) of the cells are in direct contact with the bottom surface of the carrier and not more than 20 percent (at times, no more than 10 percent or even no more than 5 percent) of the cells overlay each other (i.e., no more than the aforementioned percentage of cells lie, partially or completely, on top of one another). Further, when referring to a monolayer, it is to be understood that at least 5 percent (at times, at least 10 percent or even at least 20 percent) of the cells touch each other on the bottom surface. For some applications, a monolayer is formed in accordance with the techniques described in U.S. Pat. No. 9,329,129 to Pollak, which is incorporated herein by reference.

For some applications, prior to being imaged, the bodily sample is stained with one or more suitable dyes or stains. Optionally, the one or more suitable dyes or stains comprise one or more fluorescent dyes or stains, and the stained sample is excited under one or more suitable lighting conditions for detecting pathogens. As used herein, the term "suitable dye or stain" should be expansively construed to include any dye or stain useful for the detection of a pathogen of interest, including any suitable fluorescent dye or stain. As used herein, a "suitable fluorescent dye or stain" should be expansively construed to include a dye or stain which is capable of selectively binding to one or more types of nucleic acid (e.g., DNA only, RNA only, both DNA and RNA, etc.) and fluoresces under one or more particular lighting conditions thereby allowing for discerning of the one or more types of nucleic acids in a bodily sample. Suitable fluorescent dyes or stains can include, for example, dyes or stains that bind to DNA and do not bind to RNA, dyes or stains that bind to RNA and do not bind to DNA, and dyes or stains that bind to both DNA and RNA. Non-limiting examples of suitable fluorescent dyes or stains include, e.g., Acridine Orange, Hoechst stain, etc.

The particular lighting condition which causes a particular suitable fluorescent dye or stain to fluoresce is referred to herein as a "suitable lighting condition," which should be expansively construed to include a lighting condition which, when used to excite a particular fluorescent dye or stain, causes fluorescing of the fluorescent dye or stain. In certain embodiments, the fluorescence emitted by the excited dye or stain may be discernible through the use of one or more different light filters which enable the discerning of fluorescence within a given wavelength range. Accordingly, suitable lighting conditions may be used in view of such filters. Non-limiting examples of suitable lighting conditions include, e.g., bright field, blue light, and ultraviolet light. Additional non-limiting examples of suitable fluorescent dyes or stains and suitable lighting conditions are described in US 2012/0169863 to Bachelet and US 2015/0037806 to Pollak, both of which applications are incorporated herein by reference.

As detailed above, in certain embodiments, the sample may be stained with one or more dyes or stains that allow differentiating between RNA and DNA in the sample (i.e., differential staining). Differential staining can be accomplished, for example, by staining the sample with one or more target-specific dyes or stains. As used herein a target-specific dye or stain (e.g., a RNA-specific or a DNA-specific) is a dye or stain that under selected conditions would detectably stain the target moiety such that it may be detected in the presence of other cellular components. In this context, detectably staining a target may mean that the dye or stain binds to the target with a higher affinity than to other cellular components and/or that it provides a stronger signal (e.g. fluorescence) when associated with the target. It is noted, that some dyes or stains may stain more than one target but may be differentiated for example based on the wavelength of emitted fluorescence and/or a wavelength used for excitation of the dye or stain. In some embodiments, a target-specific dye or stain is a fluorescent dye or stain that upon binding to the target shifts its emission wavelength from an original band to a shifted band. In such cases, the target may be detected by a system configured to detect emission wavelengths within the shifted band.

Differential staining may be used to determine the relative locations of DNA and RNA, as detailed below with reference to Example 1. Optionally, a single dye or stain (e.g. Acridine Orange) may be used with different lighting conditions, to provide differential staining. Optionally, a combination of dyes or stains is used, comprising one or more DNA-specific dyes or stains (e.g., Hoechst reagent) and one or more other dyes or stains (e.g., Acridine Orange) configured to detect any nucleic acid (DNA and RNA).

For some applications, the imaging information is informative of one or more fields of the bodily sample. As used herein, a "field" is a portion of the bodily sample to be imaged. Typically, this corresponds to an area on the bottom of a sample carrier holding the sample. When the images are captured at high magnification, only a fraction of the entire blood sample can be imaged at one time. Therefore, pathogen detection system 10 virtually sub-divides an area to be imaged into a plurality of fields, and each field is imaged separately, thereby obtaining a plurality of images informative of the bodily sample, each image informative of a respective field. Optionally, the imaged fields do not overlap, or their degree of overlap is less than 5 percent or less than 1 percent of the area. In certain embodiments, each field to be imaged is imaged under one or more different lighting conditions. Optionally, an image of each field is captured a plurality of times at different lighting conditions. For example, the field may be imaged at least once in lighting conditions to detect RNA-related fluorescence, at least once in lighting conditions to detect DNA-related fluorescence, and at least once in brightfield.

Figure 3:
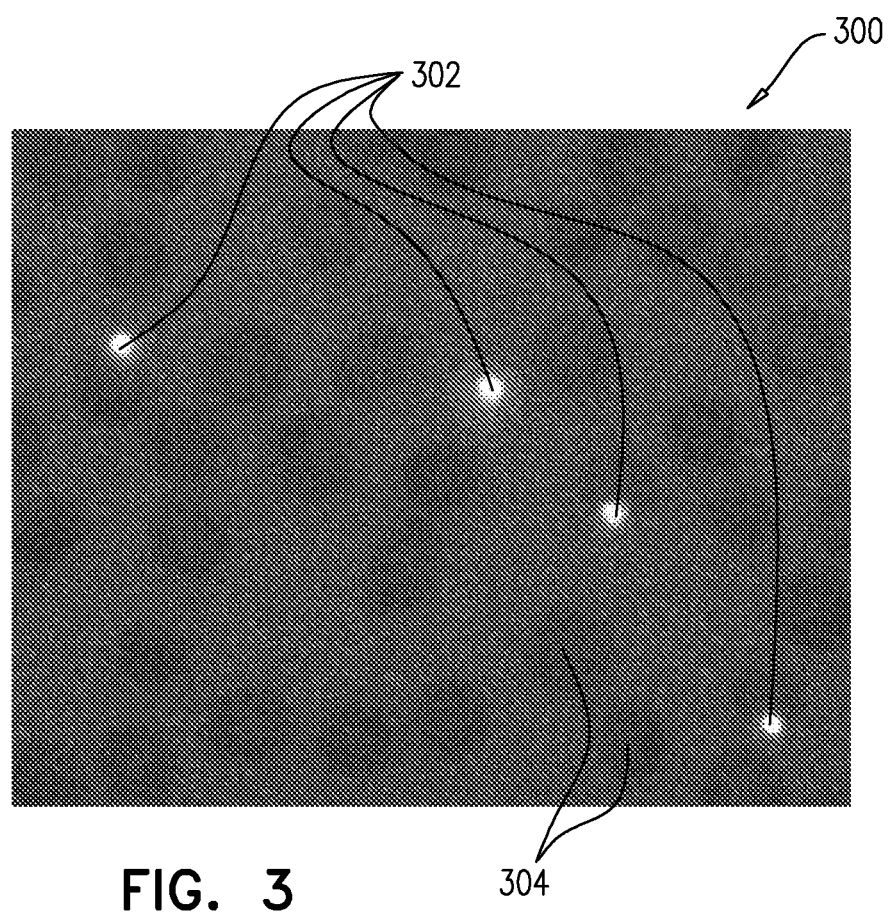
FIG. 3 is a non-limiting example of imaging information that is analyzed, in accordance with some applications of the present invention.

Reference is now made to FIG. 3, which shows, by way of non-limiting example, imaging information 300 consisting of a field of a blood sample stained with one or more suitable fluorescent dyes and excited under a suitable lighting condition, in accordance with some applications of the present application. As may be observed, due to the dye(s), constituent elements 302 fluoresce, thereby appearing brighter (or, in some cases, a different color) than other non-fluorescing constituent elements 304 (which in this case include red blood cells) in the sample and allowing for discerning of stained regions in the sample, some features of which may be informative of some specific cell types in the sample.

In certain embodiments, the imaging information is informative of one or more sample constituent elements, including candidates (i.e., constituent elements that exhibit characteristics that indicate that they may be pathogens, and are therefore candidates for being pathogens) and non-candidates. For some applications, an element is identified as a candidate based upon the element appearing fluoresced when the sample is stained with a suitable fluorescent dye or stain and is excited by a suitable lighting condition, for example, as described in US 2012/0169863 to Bachelet, and/or in US 2015/0037806 to Pollak, both of which applications are incorporated herein by reference. Alternatively or additionally, an element may be identified as a candidate based upon other criteria, such as its size shape, color, proximity to other elements, etc. As used herein, the term "non-candidate" should be expansively construed to cover a sample constituent element that is not a candidate.

Referring again to FIG. 2, in step 201, processor 28 extracts from the one or more images, from the imaging information, and/or a portion thereof, one or more sample-informative features of the bodily sample that are indicative of contextual information related to the bodily sample. Typically, a plurality of sample-informative features are extracted. As used herein, "sample-informative features" include features of the bodily sample which are not directed to a specific candidate and are usable to provide contextual information that can be used to determine the presence, likelihood of, or characteristics of a pathogenic infection in the sample, including, in some embodiments, the classification of specific candidates. By way of non-limiting examples, sample-informative features can include, for example, features related to non-candidate constituents in the sample, or features related to the quantity and/or distribution of cells of a given type in the sample. Features related to non-candidate constituents in the sample can include, for example, size-related properties of one or more non-candidates (including relative size as compared to either an expected size, or to an observed size of one or more other cells), shape-related properties of one or more non-candidates (including relative shape as compared to either an expected shape, or to an observed shape of one or more other elements), and intensity-related properties of one or more non-candidates (including relative intensity as compared to either an expected intensity, or to an observed intensity of one or more other elements). As used herein, an "expected" value (of, for example, size, shape and/or intensity) is such value as may be known in advance of analyzing imaging information relating to a given sample. Such values include, for example, population statistic values that are known or can be calculated (for example, for all humans and/or any subgroup thereof, based, for example, on age, sex, race, ethnicity, etc.), optionally according to a specific condition (e.g. altitude, treatment of the bodily sample, etc.).

For some applications, sample-informative features include features related to the distribution of candidates or pathogens within the sample or portions thereof. For example, if the number of candidates or pathogens found in a given image (or part of an image or a group of images covering a continuous portion of the sample) is significantly higher than the number of candidates or pathogens found in other parts of the same sample, this may indicate that the high concentration of candidates or pathogens found in one part of the sample might be a result of a local effect that should not affect the diagnosis of the sample. For example, a high concentration of candidates or pathogens (e.g. a high concentration of candidates overlapping red blood cells) in one part of the sample, but not in other parts, can be indicative of contamination, e.g., from a drop of blood from another sample that entered the sample under investigation.

For some applications, some or all of step 201 is performed in a pre-processing stage in order to determine, for example, whether some of the imaging information is of poor quality as measured by predetermined criteria (e.g., brightness, focus, etc.), in which case portions of the imaging information may be excluded from further processing (for example, as described hereinbelow with reference to Example 6).

In step 202, computer processor 28 identifies one or more constituent elements within the sample as being candidates of a pathogen. As described hereinabove, an element may be identified as a candidate based upon the element appearing fluoresced when the sample is stained with a suitable fluorescent dye and excited by a suitable lighting condition, for example, as described in US 2012/0169863 to Bachelet, and/or in US 2015/0037806 to Pollak, both of which applications are incorporated herein by reference. Alternatively or additionally, an element may be identified as a candidate based upon other criteria, such as shape, size, proximity to other elements (such as red blood cells, or other candidates), etc.

In step 203, computer processor extracts from the one or more images, from the imaging information, or/or from a portion thereof, one or more candidate-informative features associated with one or more identified candidates. Typically, for each candidate, a plurality of candidate-informative features are extracted. As used herein, "candidate-informative features" include features of the candidate (or, in some cases, constituent elements in close proximity to the candidate, as will be detailed below) useable to provide information for determining the likelihood of the given candidate being a pathogen or a part of a pathogen.

By way of non-limiting example, candidate-informative features can include features related to: a size of a candidate, a shape of a candidate, a motion of a candidate (based, for example, on a comparison of at least two at least partially overlapping images captured in sequence), and/or an intensity of a candidate.

For some applications, candidate-informative features include a relative location of a candidate with respect to other sample constituents (e.g., a red blood cell). Alternatively or additionally, candidate-informative features include a property of a cell (e.g. red blood cell) that at least partially overlaps with the candidate (and, optionally, also the amount of overlap), such as a size or shape of cell overlapping the candidate. For some applications, features related to size and shape of a cell overlapping the candidate include a relative size and relative shape of the overlapping cell as compared to an expected size or expected shape. As used herein, a cell is considered to overlap with a candidate at least partially if, in the imaging information, at least a portion of the cell appears to be co-located with at least a portion of the candidate (e.g., at least 20 percent or at least 25 percent of the candidate).

Optionally, candidate-informative features can include features of other constituent elements (e.g., pathogen candidates and/or pathogens) that are found in close proximity to the candidate. In this context, "close proximity" can be predefined according to any suitable metric. For example, constituents in close proximity to the candidate may include constituents located within a distance of up to 2X away from the candidate, where X is an expected (e.g., average) red blood cell diameter. Accordingly, in some embodiments, candidate-informative features (including features of the candidate, of a cell overlapping the candidate, and/or features of other constituents) may include or be limited to features that are within close proximity to the candidate.

For some applications, the imaging information or a portion thereof is processed for candidate-informative feature extraction at least partly in a pre-processing stage. In certain embodiments, the pre-processing stage can include extracting sample-informative features to obtain contextual information, and determining the imaging information which is used to extract candidate-informative features in accordance with the obtained contextual information. For some applications, the portion of the imaging information which is used for extracting candidate-informative features and the portion of the imaging information which is used for extracting sample-informative features partially or completely overlaps.

It should be noted that steps 201, 202 and 203 can be performed in any order. In accordance with some applications, steps 201, 202 and 203 are performed as a single step and/or are intertwined with one another. For some applications, some or all of steps 201, 202 and 203 are performed as a plurality of distinct steps.

Typically, based upon the candidate-informative feature(s) in combination with the sample-informative feature(s), computer processor 28 classifies a likelihood of the bodily sample being infected with a pathogenic infection. For some applications, the pathogenic infection is detected by implementing the additional steps indicated in FIG. 2.

For some applications, once at least some candidate-informative features are extracted, in step 205, processor 28 classifies the likelihoods of respective candidates being pathogens, in accordance with the candidate data obtained for each respective candidate. As used herein, the term "likelihood of being a pathogen" should be expansively construed to cover either a binary determination (e.g., either a pathogen or a non-pathogen) or a scalar determination (e.g., a number, the value of which reflects the estimated likelihood that the given candidate is a pathogen). In certain embodiments, processor 28 classifies the likelihoods of respective candidates being pathogens using the extracted sample-informative features (e.g., the features extracted in step 201) in combination with the candidate-informative features, as will be further detailed below, for example, with reference to Examples 1 and 2. This is indicated by the dashed arrow connecting step 201 to step 205, indicating that step 201 is an optional input into step 205.

Typically, subsequent to candidate classifying (i.e., step 205), in step 207, processor 28 classifies a likelihood of the bodily sample being infected with a pathogenic infection. As used herein, the term "likelihood of the bodily sample being infected" should be expansively construed to cover either a binary determination (e.g. either infected or clean) or a scalar determination (e.g. a number, the value of which reflects the estimated likelihood that the given sample is infected). For some applications, processor 28 classifies the sample based on the classification of the candidates (extracted in step 205), in combination with the sample-informative features (extracted in step 201), as will be further detailed below, for example, with reference to Examples 1 and 3.

For some applications, in step 209, processor 28 classifies the pathogenic infection as containing one or more given types of pathogen, in accordance with one or more extracted sample-informative features and/or candidate-informative features. Classifying the pathogenic infection as containing one or more given types of pathogen may be performed using information and/or features that were obtained in one or more of steps 201, 203, 205, and 207, and/or by performing one or more additional steps of feature extraction and classification. For some applications, in order to classify the pathogenic infection, (a) candidates are classified as given types of pathogens, and (b) the overall pathogenic infection is classified based upon the classifications of the individual candidates. For some applications, sample-informative features are used for classifying the individual candidates as given types of pathogens, and/or for classifying the overall infection as containing given types of pathogens.

For some applications, classifying the pathogenic infection as containing one or more given types of pathogen includes, for example, classifying the pathogenic infection in order to determine species or strains of pathogens contained within the sample, for example, as further detailed below with reference to Examples 4 and 5. Such determination may include or be limited to classifying the pathogen to a single species or strain, or to a group of several possible species or strains (at least one of which is contained within the sample) and/or ruling out a given species or strain (as a species that is not contained within the sample). For some applications, processor 28 classifies the pathogenic infection as containing one or more of *Plasmodium*, a given strain of *Plasmodium*, *Plasmodium* of a given age, and/or *Plasmodium* of a given age range.

For some applications, the computer processor generates an output to the user (e.g., on the output device) indicating whether or not the sample is infected with a pathogen, and indicating a classification of the infection. For some applications, the computer processor generates an output indicating that the presence of an infection within the bodily sample could not be determined with a sufficient degree of reliability, indicating that a portion of the sample should be re-imaged, and/or indicating that a portion of the sample should be re-imaged using different settings (e.g., using different lighting, using a different stain, using a different or new sample preparation method, and/or using different microscope settings). For some applications, in response to determining that the presence of an infection within the bodily sample could not be determined with a sufficient degree of reliability, the computer processor generates an output indicating that the user should take appropriate user actions (e.g., prepare a new sample, and/or test the sample using an independent method, etc.). Alternatively or additionally, the computer processor automatically drives the microscope system to re-image a portion of the sample, drives the microscope system to re-image a portion of the sample using different settings (e.g., different focus, or different field size), and/or modulates a frame rate at which microscope images are acquired by the microscope system.

It is noted that, for some applications, sample-informative features are not necessarily derived directly from the images. For example, sample-informative features may include statistical or other information regarding the candidates and/or other entities within the sample, and/or general characteristics of the sample. In general, the scope of the present application includes analyzing a sample on two levels, first on a candidate-by-candidate level, and then on a more general level that is indicative of characteristics of the sample as a whole.

For some applications, based upon candidate-level features, two or more sample-informative features related to the bodily sample are extracted, and a characteristic of the bodily sample is determined, by processing the two or more sample-informative features. Typically, at least some of the candidates are pathogen candidates, and candidate-informative features relating to the pathogen candidates are extracted. For some applications, candidates of entities such as reticulocytes and/or platelets are additionally identified, and candidate-informative features relating to these candidates are extracted. For some applications, the sample-informative features include a number of pathogen candidates in the sample, type of pathogen candidates in the sample, brightness of the candidates relative to background brightness, a probability of candidates being pathogens, number of candidates that have a probability of being a pathogen that exceeds a threshold, number of candidates that have a probability of being a given type of pathogen that exceeds a threshold, a number of platelets in the sample, brightness of platelets, a number of reticulocytes in the sample, a number of reticulocytes infected by pathogens in the sample, a proximity of the candidates to red blood cells, and/or a number of red blood cells in the sample.

In embodiments of the presently disclosed subject matter, fewer, more and/or different stages than those shown in FIG. 2 may be executed. In embodiments of the presently disclosed subject matter, one or more stages illustrated in FIG. 2 may be executed in a different order and/or one or more groups of stages may be executed simultaneously.

A number of examples detailing specific non-limiting applications of the method detailed above will now be provided in order to better understand the disclosed subject matter.

Example 1: Using Concentration of Reticulocytes as a Sample-Informative Feature for Classifying a Candidate, and/or for Classifying a Pathogenic Infection As detailed above, in certain embodiments, the sample is stained for discerning respective locations of DNA and RNA in the sample. Such staining may include, for example, using at least one DNA-specific dye and at least one RNA-specific dye, or at least one target-specific dye (either DNA or RNA) and at least one dye that stains both DNA and RNA. For some applications, in order to classify the likelihood of a candidate being a pathogen (step 205), the respective locations of RNA and DNA staining in sample are used by the processor to determine if the staining pattern(s) correspond(s) with the pattern(s) expected for a pathogen.

Figure 4:
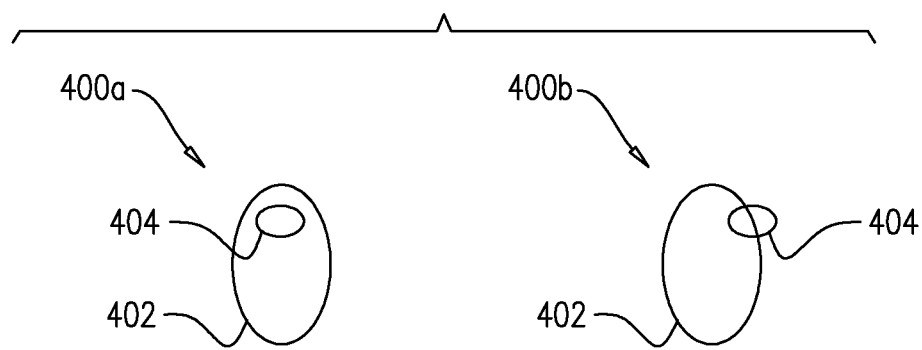
FIG. 4 is a non-limiting illustration of a relative location of an RNA-stained region and a DNA-stained region, in accordance with some applications of the present invention.

FIG. 4 schematically illustrates candidates 400a and 400b, each candidate shows an area stained for RNA (RNA portion 402) and an area stained for DNA (DNA portion 404). RNA portion 402 and DNA portion 404 may be differentially stained, e.g. using different dyes and/or different lighting, in order to discern the particular boundaries of each stained area. As is shown in FIG. 4, in candidate 400a the DNA portion 404 completely overlaps the RNA portion 402, while in candidate 400b the DNA portion 404 partially overlaps the RNA portion 402.

A candidate which appears to have at least partially overlapping DNA and RNA might be a pathogen. However, the appearance of overlapping RNA and DNA stained regions can also be caused by a different entity or entities, including, for example, a different cell type, or two separate bodies (one of which contains DNA and the other of which contains RNA) seemingly positioned on top of one another.

Mature red blood cells have no detectable DNA or RNA and therefore do not fluoresce when stained for nucleic acids. By contrast, *Plasmodium* trophozoites (which are a type of pathogen) may be detected as DNA-containing and RNA-containing bodies within red blood cells. Therefore, for some applications, in order to identify red blood cells that contain pathogens, a staining substance that stains both DNA and RNA (such as, Acridine Orange) is used. Alternatively or additionally, a stain that stains only DNA (such as a Hoechst stain) is used.

Howell Jolly bodies are DNA-containing bodies that may be found in red blood cells in some unhealthy conditions. In some cases, the presence of Howell Jolly bodies in a sample may increase the chance of false positive determination of a pathogen infection. Even if a DNA-specific stain is used in conjunction with a stain that stains both DNA and RNA, the Howell Jolly bodies may cause a false positive determination of a pathogen infection. Therefore, in some embodiments, differentiation between red blood cells that contain Howell Jolly bodies and red blood cells that contain pathogens may be beneficial.

Young red blood cells, termed reticulocytes, are sometimes found in blood. These cells contain RNA bodies only. A positive correlation is known between the presence of Howell Jolly bodies in red blood cells and a larger than normal amount of reticulocytes. Therefore, for some applications, sample-informative features include features that are indicative of a concentration of reticulocytes in a blood sample. (It is noted that a *Plasmodium* infection also raises the reticulocyte count for a patient. However, this increase (of, for example, about 5%) is typically much lower than the increase typical of patients that have a high Howell Jolly body count (which may be about ten times as great). Accordingly, a threshold for the determination of a high reticulocyte count is typically slightly higher than the average value for humans (or a given sub-population thereof).)

Based upon identifying a high concentration of reticulocytes, the likelihood of pathogen candidates being Howell Jolly bodies increases. In turn, the likelihood of the candidates being pathogens decreases, and the likelihood of the sample being infected decreases. Therefore, for some applications, the computer processor adjusts a threshold for a positive determination of an infection, based upon the concentration of reticulocytes. For example, many reticulocytes detected concomitantly with low parasitemia (e.g. less than 200 parasites/microliter blood) may be interpreted as being indicative of a high probability of a false positive (i.e., the sample being non-infected).

Alternatively or additionally, based upon the concentration of reticulocytes, in order to classify the likelihood of a candidate being a pathogen (step 205 of FIG. 2), the processor ascribes more weight to the relative positions of DNA and/or RNA within candidate given red blood cell, rather than simply the presence of DNA and/or RNA within the red blood cell. Alternatively or additionally, based upon the concentration of reticulocytes, in order to classify the likelihood of a sample being infected (step 207 of FIG. 2), the processor ascribes more weight to extracellular *Plasmodium* candidates, rather than intracellular *Plasmodium* candidates (which could be Howell Jolly bodies).

Example 2: Using Distribution of Candidates within a Sample as a Sample-Informative Feature for Classifying a Candidate Candidates within a sample are expected to be uniformly distributed. Therefore, for some applications, a distribution of candidates within the sample that differs significantly from an expected uniform distribution is used as a sample-informative feature. For example, if there are significant candidate clusters, the clusters may be foreign bodies associated with the sample carrier rather than a portion of the blood sample, or may indicate that a different infected sample contaminated the sample being analyzed (for example, by spilling over from an adjacent chamber on a sample carrier). In response to detecting a non-uniform distribution of candidate, candidates that are within localized clusters may be given a lower score (i.e., they may be classified as being less likely to be pathogens). For example, if the sample-informative features are indicative of clustering of candidates, the processor may use distance from the cluster center(s) of any given candidate as a feature for classifying the candidate.

Example 3: Platelet Concentration as a Sample-Informative Feature for Classifying a Sample as Infected Platelets typically appear as small extracellular RNA bodies, although some platelets may appear to be overlapped with cells because they are positioned on or under a cell when the sample is imaged. A normal concentration of platelets is typically between 150,000-400,000 platelets per microliter of whole blood.

It is known that the concentration of platelets may be affected by *Plasmodium* infection, its severity and the species of *Plasmodium*, as well as by other unrelated conditions (including medical conditions, treatments and medications). Accordingly, for some applications, the number and/or concentration of platelets in a sample is used as a sample-informative feature, and, for example, may be used as an input in classifying the likelihood of the sample being infected.

Example 4: Platelet Concentration as a Sample-Informative Feature Informative of a Species of Pathogen As mentioned in the context of Example 3, the number and/or concentration of platelets can be correlated with a specific species of pathogen, for example a low platelet count has been shown to be correlated with a *Plasmodium falciparum* infection to a significantly greater extent than *Plasmodium vivax* infection. For some applications, in accordance with step 209 of FIG. 2, the number and/or concentration of platelets in a blood sample is used as an input for classifying a pathogenic infection as containing a given type of pathogen.

Example 5: Red Blood Cell Size and Shape as a Sample-Informative Feature

Some pathogens change the morphology of infected cells. For example, some pathogens (e.g., relatively mature trophozoites of *Plasmodium vivax* and *Plasmodium ovale*) cause an enlargement of infected red blood cells, sometimes to about two-fold that of uninfected cells. Other pathogens (e.g., *Plasmodium malariae*) reduce the size of infected red blood cells. Still other pathogens (e.g., *Plasmodium falciparum*) do not enlarge infected cells or reduce their size. For some applications, the sizes of red blood cells that appear to be infected within a blood sample are used as a sample-informative feature that is indicative of the sample being infected (e.g., in step 207 of FIG. 2), and/or is indicative of an identity of the pathogen (e.g., in step 209 of FIG. 2).

For example, a blood sample infected by *Plasmodium vivax* and/or *Plasmodium ovale* is expected to include infected red blood cells that are significantly enlarged. A blood sample infected by *Plasmodium malariae*, on the other hand, is expected to include infected red blood cells that are significantly diminished in size. Therefore, for some applications, detection of such enlarged and/or diminished cells is used as a sample-informative feature that is indicative of the sample being infected (e.g., in step 207 of FIG. 2) and/or is indicative of an identity of the pathogen (e.g., in step 209 of FIG. 2).

In another example, *Plasmodium ovale* may cause infected red blood cells to become more oval than uninfected red blood cells that tend to appear round. Accordingly, one or more of the following sample-informative features may be interpreted as being indicative of the sample being infected and/or being infected with *Plasmodium ovale*: the presence of oval red blood cells in the sample, the presence of a higher than expected portion of oval red blood cells, and/or the presence and/or amount of infected red blood cells that appear to be oval.

Features of oval(s) (e.g., height versus width) may be used in a classification in a weighted manner. For example, the weight given to an oval feature that is close to an expected value may be higher than if the value is closer to an expected value for uninfected red blood cell or values that are significantly more deviant than the expected value for infected red blood cells (e.g., if the oval appears to be rod like).

It should be noted that a determination that an infected red blood cell (or a group of infected red blood cells), or potentially infected red blood cell, is different in any given property (e.g. size, shape, etc.) than the general population of red blood cells (or different than uninfected cells), and/or a determination of a degree of such difference, is typically reached using any acceptable statistic. For example, an average size of two groups may be used and/or an average size of one group may be used in relation to a given percentile of the other group. Optionally, a plurality of statistics is used. Optionally, one or more of the values for red blood cells (or for uninfected red blood cells) are taken from known statistics of the general population or a subgroup thereof. In some embodiments, one or more statistics of all red blood cells in the sample (or a portion thereof) may be used, rather than using only the uninfected red blood cells. For example, this may be used in cases in which the portion of infected red blood cells within the sample is sufficiently small.

Optionally, a determination that an infected or potentially infected red blood cell is different or relatively different in any given property (e.g. size, shape, etc.) is made by comparing the given property of the infected red blood cell or potentially infected red blood cell to properties of one or more clean red blood cells in the sample. As such, properties of one or more clean red blood cells can also be used as sample-informative features for determining the likelihood that a candidate is a pathogen, for determining the likelihood that a sample is infected, and/or for classifying the species of a pathogen.

It should be noted that red blood cell features (e.g., features related to red blood cell size and/or shape) can also be used in candidate classification (e.g., as a candidate-informative feature used in step 205 of FIG. 2) when compared with an expected value. By way of non-limiting example, candidates which appear to be inside (or co-located with) red blood cells that are relatively large or small than an expected value or have a shape that is different than an expected shape (e.g. oval instead of round) are more likely to be pathogens.

It should also be noted that features of red blood cells in the sample (e.g. features related to red blood cell size and/or shape) can be used in sample classification (e.g., as a sample-informative feature used in step 207 of FIG. 2). By way of non-limiting example, such features include a statistic taken for a group of red blood cells in the sample (e.g., a statistic for seemingly infected red blood cells in the sample, a statistic for uninfected red blood cells in the sample, and/or a statistic for red blood cells in the sample in general). One non-limiting example includes comparing a statistic of seemingly infected red blood cells in the sample (e.g., size) to an expected value (e.g., average size of human red blood cell) or to a corresponding statistic for red blood cells in the sample in general. When the seemingly infected red blood cells are found to be larger or smaller than the compared value, this may be used as an indication that the sample is infected.

Echinocytes are red blood cells that have abnormal cell membranes with many small, symmetrically spaced thorny projections. Acanthocytes also have thorny abnormal projections, but they are irregular and asymmetrical.

In some cases, a *Plasmodium* infection causes the appearance of echinocytes or acanthocytes. Other causes for such shapes may be other pathologies and even a prolonged exposure to some solutions (e.g., dye solutions). Additionally, some strains of *Plasmodium* cause greater deformity than other strains. For example, *Plasmodium vivax* is typically more deforming than *Plasmodium falciparum*, while each of *Plasmodium vivax* and *Plasmodium ovale* is typically more deforming than each of *Plasmodium malariae* and *Plasmodium falciparum*. Therefore, for some applications, the presence of such shapes in a sample is used as a sample-informative feature that is indicative of the sample being infected (e.g., in step 207 of FIG. 2), and/or is indicative of an identity of the pathogen (e.g., in step 209 of FIG. 2).

In some strains of *Plasmodium*, there is a positive correlation between a degree of red blood cell deformity and the age of the infecting pathogens. Therefore, for some applications, the presence of such shapes in a sample is used as a sample-informative feature that is indicative of the age of the detected pathogens (e.g., in step 209 of FIG. 2).

Example 6: Using Staining Quality as a Sample-Informative Feature

Staining of a biological sample is known to be a time dependent process. Once cells are exposed to a dye it takes time for the dye to penetrate the cells and reach its target site(s) within the cells. During this period, staining may become sharper and/or more localized with sharper intensity gradients (especially if the sample is not washed before being imaged). Typically, this process follows a saturation curve. In a first phase, staining increases relatively fast until some degree of staining is reached (i.e., a fast staining phase). Thereafter, quality still increases but relatively slowly for another period of time (i.e., a slow staining phase). At a later time, staining quality may deteriorate, for example, due to photo bleaching (in a fluorescent dye), and/or due to the dye slowly diffusing through the sample, away from the target(s).

For some applications, imaging a plurality of fields (e.g., 200 fields or more, at least some of which may be imaged more than once) of a bodily sample, such as a blood sample, may take a few minutes (e.g., 2-3 minutes or more). For Hoechst staining (which is used, for example, in the detection of *Plasmodium* infection), the fast staining phase may take 30 minutes or more.

Accordingly, when imaging a plurality of fields is carried out over the above-described time scale, there might be a significant variation in staining quality between fields. This variation may affect the diagnostic result (e.g., by changing an intensity value, an intensity gradient value, and/or a threshold for infection). For some applications, in order to account for the variation in staining quality, staining quality of the sample is used as a sample-informative feature, in accordance with techniques described herein.

For some applications, an average staining quality across a plurality images is determined, and a staining quality parameter for each image is determined, based on the image's relative staining quality compared to the average value. The staining quality parameter can be used as a sample-informative feature, for example, for discarding, from being used in further analysis, images that were taken too early or too late, when staining is not sufficiently informative for diagnostics. Alternatively or additionally, the staining quality parameter can be used to adjust one or more thresholds for different fields or groups of fields based on the staining quality parameter, and/or introduce the staining quality parameter into the classifying of candidates, so that candidates from a plurality of fields having different staining qualities can be compared. For example, the candidate classification can be normalized using the staining quality.

For some applications, in response to the staining quality parameter, a frame rate at which images of the bodily sample are acquired is modulated. For example, in response to detecting that the staining is of a low quality, images may be acquired at a greater frame rate, and vice versa. Alternatively or additionally, in response to the staining quality parameter, the number of times each field is imaged is modulated. In general, the scope of the present invention includes using sample-informative features as an input for discarding some images from being used, for modulating a frame rate at which images are acquired, and/or for modulating the number of times that each imaging field is imaged.

Optionally, when using two or more stains, the staining quality variation may differ between the stains. For example, Acridine Orange staining may be complete, when Hoechst staining is still in the fast staining phase. Accordingly, for some applications, the staining quality parameter is treated separately for each stain, and/or the relative staining quality between the stains may be used as a staining quality parameter.

Example 7: Using Affinity of Candidates for Reticulocytes as a Sample-Informative Feature

*Plasmodium vivax* and *Plasmodium ovale* have an affinity for infecting reticulocytes, over mature red blood cells. Conversely, *Plasmodium falciparum* infects all red blood cells equally, while *Plasmodium malariae* has an affinity for mature red blood cells. Accordingly, for some applications, a relationship between the number of pathogen candidates associated with reticulocytes and the number of candidates associated with mature red blood cells is determined, and this is used as a sample-informative feature.

As described hereinabove, for some applications, in accordance with step 209 of FIG. 2, the processor classifies a pathogen as containing a given type of pathogen. For some applications, once it is determined that a sample is infected, the processor classifies the pathogen as containing a given type of pathogen, based upon the estimated ages of infected red blood cells, and/or based upon a relationship between the number of pathogen candidates associated with reticulocytes and the number of candidates associated with mature red blood cells. For example, if the pathogens have an affinity for reticulocytes, this may be used as an indication that that the detected pathogen is *Plasmodium vivax*. Alternatively, an essentially uniform distribution of the pathogen in red blood cells of all ages (proportional to relative abundance of the differently-aged red blood cells) may be used as an indication that that the detected pathogen is *Plasmodium falciparum*.

Example 8: Using Detection of Contamination as a Sample-Informative Feature

An image of a blood sample may contain foreign objects that are irrelevant for diagnosis and may be due for example to dirt or flaws in a solution or tool used to prepare or hold the blood sample (e.g., a dilution solution and/or a sample chamber used for housing the sample). Such objects may include objects that appear similar to a pathogen and/or objects that are dissimilar to a pathogen.

For some applications of the present invention, the computer processor is configured to extract, from the one or more images, at least one sample-informative feature that is indicative of contextual information related to the bodily sample. At least partially based upon the extracted sample-informative feature, the computer processor identifies that there is a defect associated with the bodily sample disposed in the sample carrier, and classifies a source of the defect (for example, as being the sample carrier, a given portion of the sample carrier, the sample itself, and/or a diluent in which the sample has been diluted). The computer processor generates an output on the output device that is indicative of the source of the defect.

For example, such an output may be generated based upon a sample-informative feature that is indicative of the presence of foreign objects within the sample. The source of the foreign objects is expected to affect their concentration and distribution in the sample. For example, if the source is the blood sample itself, then the amount of foreign objects that is detected is typically proportional to the size of the sample. For some applications, in response to detecting foreign objects having this characteristic, a threshold for diagnosis is adjusted. For example, the threshold for the number of pathogens within a sample that is sufficient to deem the sample to be infected may be a function of a relationship between the concentration of foreign objects within the sample, to that of red blood cells.

For some applications, the processor is configured to determine that the source of foreign objects is limited to a given chamber, a given set of chambers, a given field, or a given set of fields. For such cases, the computer processor may ascribe lower weight to features that are detected in the affected chambers or fields, and/or may use data from other chambers or fields as inputs to analyzing features detected in the affected chambers and fields.

For some applications, the computer processor is configured to detect that the source of foreign objects is a diluent in which the sample has been diluted (for example, in response to detecting foreign objects with characteristics that are common to a plurality of samples and/or chambers). In such cases, the processor may generate an output indicating the likely source of the foreign objects. For some applications, the computer processor is configured to detect cross-contamination between chambers, and to generate an output indicating that this is the case.

It is noted that although some applications of the present invention have been described with respect to detecting a pathogen infection within a bodily sample, the scope of the present invention includes performing similar techniques with respect to identifying other components or entities within a bodily sample. For example, similar techniques to those described herein may be used for detecting the concentration of a given entity within a blood sample, by (a) extracting one or more candidate-informative features associated with an element that is a candidate of the given entity, (b) extracting one or more sample-informative feature that are indicative of contextual information related to the bodily sample, and (c) processing the candidate-informative feature in combination with the sample-informative feature. For some applications, the sample is a sample that includes blood, and the candidates are candidates of entities within the blood, such as platelets, white blood cells, anomalous white blood cells, circulating tumor cells, red blood cells, reticulocytes, Howell Jolly bodies, etc. For some such applications, a blood count (e.g., a complete blood count) is performed by identifying such candidates, and performing techniques as described herein.

For some applications, the sample is a different bodily sample, and the techniques described herein are used for identifying a pathogen infection within the sample. For example, the techniques described herein may be used to identify Mycobacterium tuberculosis within a sample of sputum. Alternatively or additionally, the sample is a different bodily sample, and the techniques described herein are used for identifying abnormal cells within the sample. For example, the techniques described herein may be used to identify cancerous cells in a PAP smear or in a urine sample.

In general, it is noted that although some applications of the present invention have been described with respect to a blood sample, the scope of the present invention includes applying the apparatus and methods described herein to a variety of samples. For some applications, the sample is a bodily sample, such as, blood, saliva, semen, sweat, sputum, vaginal fluid, stool, breast milk, bronchoalveolar lavage, gastric lavage, tears and/or nasal discharge. The bodily sample may be from any living creature, and is typically from warm blooded animals. For some applications, the bodily sample is a sample from a mammal, e.g., from a human body. For some applications, the sample is taken from any domestic animal, zoo animals and farm animals, including but not limited to dogs, cats, horses, cows and sheep. Alternatively or additionally, the bodily sample is taken from animals that act as disease vectors including deer or rats.

For some applications, similar techniques to those described hereinabove are applied to a non-bodily sample. For some applications, the sample is an environmental sample, such as, water (e.g. groundwater) sample, surface swab, soil sample, air sample, or any combination thereof. In some embodiments, the sample is a food sample, such as, a meat sample, dairy sample, water sample, wash-liquid sample, beverage sample, and any combination thereof.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that blocks of the flowchart shown in FIG. 2 and combinations of blocks in the flowchart, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIG. 2, computer processor 28 typically acts as a special purpose sample-analysis computer processor. Typically, the operations described herein that are performed by computer processor 28 transform the physical state of memory 30, which is a real physical article, to have a different magnetic polarity, electrical charge, or the like depending on the technology of the memory that is used.

Unless specifically stated otherwise, as apparent from the discussions herein, throughout the specification discussions utilizing terms such as "processing,", "executing," "obtaining," "determining," "classifying," "storing," "selecting," or the like, refer to the action(s) and/or process(es) of a computer that manipulate and/or transform data into other data, said data represented as physical, such as electronic, quantities and/or said data representing the physical objects. The terms "computer" and "processor" should be expansively construed to cover any kind of electronic device with data processing capabilities including, by way of non-limiting example, the system disclosed in the present application.

It is to be understood that the term "non-transitory" is used herein to exclude transitory, propagating signals, but to include, otherwise, any volatile or non-volatile computer memory technology suitable to the presently disclosed subject matter.

Typically, computer processor generates an output on output device 34. The output may be provided in any acceptable form, including a graph, graphic or text displayed on a monitor of a control unit, a printout, as a voice message, or on a user's smartphone display, for accepting processed data from the processing utility and displaying information relating to the structural features obtained and/or associated values determining the presence and optionally the identity of a pathogenic infection, using lists, tables, graphs etc. The output device may include a monitor that is connected to a printer for printing the output.

User interface 32 may be used to control the operation of system 10 and/or computer processor 28, including, inter alia, inputting data with respect to the examined bodily sample (e.g., source, date, place, etc.), controlling conditions of operating the system, types of dyes used, number of images to be taken, time interval between images, etc.

At times, image analysis by the computer processor may involve adjustment or normalization of image brightness on the basis of degree of staining of the sample. These may be based on, for example, identifying one or more of brightest and/or dimmest pixel values in the image or set of image (for example, corresponding to a particular sample), average brightness of brightest and/or dimmest area, and/or image histogram. Such features may be extracted from a representative image (not necessarily the one being normalized) or from statistical analysis of multiple images. The features used for normalization may be based on a single or multiple images, which may be captured using different excitation wavelengths (e.g., Acridine Orange providing different colors under different illumination wavelengths). Image brightness may also be adjusted using other control means, such as image capturing component exposure time and/or brightness of illumination.

The conditions of microscope system 11 may be such as to control the timing of the image acquisition, e.g., to allow sufficient incubation time with the one or more dyes or stains as well as the operation with different optical configurations of excitation and/or emission wavelengths, in order to image the stained sample at various colors or fluorescence spectra.

The components of the pathogen detection system, namely, imaging module 14, computer processor 28, output device 34, etc. may be directly connected to each other (e.g., directly by a wire) or one or more of the components may be remote from one or more other components. For example, the imaging module may send data to computer processor 28 over an intranet or over the internet, to allow processing at a remote location.

Examples of systems which may be used for performing the techniques of the present disclosure are described in WO 2012/090198 to Bachelet and in US 2014/0347459 to Greenfield, both of which applications are incorporated herein by reference.

There is therefore provided the following inventive concepts, in accordance with some applications of the present invention:

Inventive concept 1. A method of detecting a pathogenic infection in a bodily sample, the method comprising:

storing in a memory imaging information related to the bodily sample, at least a portion of the imaging information being informative of one or more pathogen candidates in the sample, providing, by a processor operatively coupled to the memory, a first processing of a first part of the imaging information, the first processing including: extracting at least one sample-informative feature, and processing the extracted at least one sample-informative feature to obtain context data indicative of contextual information related to the sample, providing, by the processor, a second processing of a second part of the imaging information, the second processing including: identifying at least one pathogen candidate in the sample; extracting at least one candidate-informative feature associated with the identified candidate, and processing the at least one extracted candidate-informative feature to obtain candidate data indicative of at least one classifying property of the candidate, providing, by the processor, a first classifying, the first classifying including classifying the at least one identified candidate as a pathogen or a non-pathogen at least in accordance with the obtained candidate data, providing, by the processor, a second classifying, the second classifying including classifying the sample as infected or clean at least in accordance with the results of the first classifying and the obtained context data, wherein a pathogenic infection in the bodily sample is determined based on the results of the second classifying.

Inventive concept 2. The method of inventive concept 1 wherein the first classifying is performed further in accordance with the obtained context data.

Inventive concept 3. The method of inventive concept 1 wherein the second classifying is performed further in accordance with the obtained candidate data for at least one identified candidate.

Inventive concept 4. The method of any one of inventive concepts 1-3, further comprising providing, by the processor, classifying at least one pathogen in the sample at least in accordance with the obtained context data.

Inventive concept 5. The method of inventive concept 4, wherein classifying the at least one pathogen includes determining the species of the at least one pathogen.

Inventive concept 6. The method of any one of inventive concepts 1-5, wherein the at least one candidate-informative feature is selected from the group consisting of a feature related to: a size of the candidate, a shape of the candidate, a motion of the candidate, an intensity of the candidate, a location of the candidate within the sample, and a property of a cell overlapping the candidate.

Inventive concept 7. The method of inventive concept 6, wherein the cell is a red blood cell, and the property includes at least one of: a size related property and a shape related property.

Inventive concept 8. The method of any one of inventive concepts 1-7, wherein the at least one sample-informative feature is selected from the group consisting of a feature related to: a size, shape, or intensity of one or more non-candidate constituents in the sample, a quantity of cells of a given cell type, a distribution of cells of a given cell type, and a distribution of candidates.

Inventive concept 9. The method of any one of inventive concepts 1-8, wherein the bodily sample is selected from a blood sample, a diluted blood sample, a sample comprising predominantly red blood cells and a diluted sample comprising predominantly red blood cells.

Inventive concept 10. A method of detecting a pathogen in a bodily sample, the method comprising:

storing in a memory imaging information related to the bodily sample, at least a portion of the imaging information being informative of one or more pathogen candidates in the sample, providing, by a processor operatively coupled to the memory, a first processing of a first part of the imaging information, the first processing including: extracting at least one sample-informative feature, and processing the extracted at least one sample-informative feature to obtain context data indicative of contextual information related to the sample, providing, by the processor, a second processing of a second part of the imaging information, the second processing including: identifying at least one pathogen candidate in the sample; extracting at least one candidate-informative feature associated with the identified candidate, and processing the at least one extracted candidate-informative feature to obtain candidate data indicative of at least one classifying property of the candidate, providing, by the processor, a first classifying, the first classifying including classifying the at least one identified candidate as a pathogen or a non-pathogen at least in accordance with the obtained candidate data and the obtained context data.

Inventive concept 11. The method of inventive concept 10 further comprising:

providing, by the processor, a second classifying, the second classifying including classifying at least one pathogen in the sample at least in accordance with the obtained candidate data.

Inventive concept 12. The method of inventive concept 11, wherein the second classifying includes determining the species of the at least one pathogen.

Inventive concept 13. The method of any one of inventive concepts 10-12, further comprising: providing, by the processor, a pre-processing of the imaging information, the pre-processing including determining the imaging information to be included in at least one of the first part and the second part, wherein the pre-processing includes extracting at least one sample-informative feature from the imaging information, and processing the extracted at least one sample-informative feature to obtain context data indicative of contextual information related to the sample, and wherein the determining is made in accordance with the obtained context data.

Inventive concept 14. The method of any one of inventive concepts 10-13, wherein the at least one candidate-informative feature is selected from the group consisting of a feature related to: a size of the candidate, a shape of the candidate, a motion of the candidate, an intensity of the candidate, a location of the candidate within the sample, and a property of a cell overlapping the candidate.

Inventive concept 15. The method of inventive concept 14 wherein the cell is a red blood cell, and the property includes at least one of: a size related property and a shape related property.

Inventive concept 16. The method of any one of inventive concepts 10-15, wherein the at least one sample-informative feature is selected from the group consisting of a feature related to: a size, shape, or intensity of one or more non-candidate constituents in the sample, a quantity of cells of a given cell type, a distribution of cells of a given cell type, and a distribution of candidates.

Inventive concept 17. The method of any one of inventive concepts 10-16, wherein the bodily sample is selected from a blood sample, a diluted blood sample, a sample comprising predominantly red blood cells and a diluted sample comprising predominantly red blood cells.

Inventive concept 18. A system for detecting a pathogenic infection in a bodily sample, comprising:
  a memory operatively coupled to a digital microscope and configured to store imaging information captured by the digital microscope, the imaging information related to a bodily sample, at least a portion of the imaging information being informative of one or more pathogen candidates in the sample; and
  a processor operatively coupled to the memory and configured to:
    process, in a first processing, a first part of the imaging information, the first processing including: extracting at least one sample-informative feature, and processing the extracted at least one sample-informative feature to obtain context data indicative of contextual information related to the sample,
    process, in a second processing, a second part of the imaging information, the second processing including: identifying at least one pathogen candidate in the sample; extracting at least one candidate-informative feature associated with the identified candidate, and processing the at least one extracted candidate-informative feature to obtain candidate data indicative of at least one classifying property of the candidate,
    classify, in a first classifying, the at least one identified candidate as a pathogen or a non-pathogen at least in accordance with the obtained candidate data,
    classify, in a second classifying, the sample as infected or clean at least in accordance with the results of the first classifying and the obtained context data,
  wherein a pathogenic infection in the bodily sample is determined based on the results of the second classifying.

Inventive concept 19. The system of inventive concept 18, wherein the first classifying is performed further in accordance with the obtained context data.

Inventive concept 20. The system of any one of inventive concepts 18 or 19, wherein the second classifying is performed further in accordance with the obtained candidate data for at least one identified candidate.

Inventive concept 21. The system of any one of inventive concepts 18-20, wherein the processor is further configured to, prior to the first and second processing:
  pre-process the imaging information, the pre-processing including determining the imaging information to be included in at least one of the first part and the second part, wherein the pre-processing includes extracting at least one sample-informative feature from the imaging information, and processing the extracted at least one sample-informative feature to obtain context data indicative of contextual information related to the sample, and wherein the determining is made in accordance with the obtained context data.

Inventive concept 22. The system of any one of inventive concepts 18-21, wherein the processor is further configured to classify a pathogen in the sample at least in accordance with the obtained context data.

Inventive concept 23. The system of any one of inventive concepts 18-22, wherein the at least one candidate-informative feature is selected from the group consisting of a feature related to: a size of the candidate, a shape of the candidate, a motion of the candidate, an intensity of the candidate, a location of the candidate within the sample, and a property of a cell overlapping the candidate.

Inventive concept 24. The system of inventive concept 23, wherein the cell is a red blood cell, and the property includes at least one of: a size related property and a shape related property.

Inventive concept 25. The system of any one of inventive concepts 18-24, wherein the at least one sample-informative feature is selected from the group consisting of a feature related to: a size, shape, or intensity of one or more non-candidate constituents in the sample, a quantity of cells of a given cell type, a distribution of cells of a given cell type and a distribution of candidates.

Inventive concept 26. The system of any one of inventive concepts 18-25, wherein the bodily sample is selected from a blood sample, a diluted blood sample, a sample comprising predominantly red blood cells and a diluted sample comprising predominantly red blood cells.

Inventive concept 27. A computer program product implemented on a non-transitory computer usable medium having computer readable program code embodied therein to cause the computer to perform a method of detecting a pathogenic infection in a bodily sample, the method comprising:
  storing in a memory comprised in or operatively coupled to the computer, imaging information related to the bodily sample, at least a portion of the imaging information being informative of one or more pathogen candidates in the sample,
  providing, by a processor comprised in or operatively coupled to the computer, and operatively coupled to the memory, a first processing of a first part of the imaging information, the first processing including: extracting at least one sample-informative feature, and processing the extracted at least one sample-informative feature to obtain context data indicative of contextual information related to the sample,
  providing, by the processor, a second processing of a second part of the imaging information, the second processing including: identifying at least one pathogen candidate in the sample; extracting at least one candidate-informative feature associated with the identified candidate, and processing the at least one extracted candidate-informative feature to obtain candidate data indicative of at least one classifying property of the candidate,
  providing, by the processor, a first classifying, the first classifying including classifying the at least one identified candidate as a pathogen or a non-pathogen at least in accordance with the obtained candidate data, and
  providing, by the processor, a second classifying, the second classifying including classifying the sample as infected or clean at least in accordance with the results of the first classifying and the obtained context data.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a microscope system configured to acquire one or more microscope images of a bodily sample selected from the group consisting of: a blood sample, a diluted blood sample, a sample comprising predominantly red blood cells, and a diluted sample comprising predominantly red blood cells;
   an output device; and
   at least one computer processor configured to:
      identify, in the one or more images, at least one element as being a pathogen candidate,
      extract, from the one or more images, at least one candidate-informative feature associated with the pathogen candidate,
      extract, from the one or more images, at least one sample-informative feature that is indicative of contextual information related to the bodily sample, the sample-informative feature being selected from the group consisting of: an indication of a presence of Howell Jolly bodies within the bodily sample, a concentration of platelets within the bodily sample, a relationship between a number of reticulocytes associated with candidates and a number of mature red blood cells associated with candidates, and a concentration of reticulocyte bodies within the bodily sample;
      determining a likelihood of the bodily sample being infected with a pathogenic infection, by processing the candidate-informative feature in combination with the sample-informative feature, and
      generate an output upon the output device, in response thereto.

2. The apparatus according to claim 1, wherein:
   the microscope system is configured to acquire one or more microscope images of the selected bodily sample, by acquiring one or more microscope images of a bodily sample that is stained with a stain; and
   the at least one computer processor is configured to identify at least one element as being a pathogen candidate by identifying the at least one element as being a pathogen candidate by identifying that the at least one element is stained.

3. The apparatus according to claim 1, wherein the at least one computer processor is configured to process the candidate-informative feature in combination with the sample-informative feature by:
   in response to the candidate-informative feature, performing a first determining step, in which a likelihood of the pathogen candidate being a pathogen is determined, and
   in response to the first determining step in combination with the sample-informative feature, performing a second determining step in which a likelihood of the bodily sample containing a pathogenic infection is determined.

4. The apparatus according to claim 1, wherein the at least one computer processor is configured to process the candidate-informative feature in combination with the sample-informative feature by:
   in response to the candidate-informative feature in combination with the sample-informative feature, performing a first determining step, in which a likelihood of the pathogen candidate being a pathogen is determined, and
   at least partially in response to the first determining step, performing a second determining step, in which in which a likelihood of the bodily sample containing a pathogenic infection is determined.

5. The apparatus according to claim 1, wherein the at least one computer processor is configured to extract, from the one or more images, at least one candidate-informative feature associated with the pathogen candidate by extracting, from the one or more images, at least one candidate-informative feature associated with the pathogen candidate, the candidate-informative feature being a feature selected from the group consisting of: a size of the pathogen candidate, a shape of the pathogen candidate, a motion of the pathogen candidate, an intensity of the pathogen candidate, a location of the pathogen candidate within the bodily sample, a property of a cell overlapping the pathogen candidate, a color of the pathogen candidate, a texture of the pathogen candidate, and a sharpness of a boundary of the pathogen candidate.

6. The apparatus according to claim 1, wherein the at least one computer processor is configured to extract, from the one or more images, at least one sample-informative feature that is indicative of contextual information related to the bodily sample by extracting, from the one or more images, the indication of the presence of Howell Jolly bodies within the bodily sample.

7. The apparatus according to claim 1, wherein the at least one computer processor is configured to extract, from the one or more images, at least one sample-informative feature that is indicative of contextual information related to the bodily sample by extracting, from the one or more images, the concentration of platelets within the bodily sample.

8. The apparatus according to claim 1, wherein the at least one computer processor is configured to extract, from the one or more images, at least one sample-informative feature that is indicative of contextual information related to the bodily sample by extracting, from the one or more images, the relationship between the number of reticulocytes associated with candidates and the number of mature red blood cells associated with candidates.

9. The apparatus according to claim 1, wherein the at least one computer processor is configured to extract, from the one or more images, at least one sample-informative feature that is indicative of contextual information related to the bodily sample by extracting, from the one or more images, the concentration of reticulocyte bodies within the bodily sample.

10. The apparatus according to claim 9, wherein the at least one computer processor is configured to determine the likelihood of the bodily sample being infected with the pathogenic infection by adjusting a threshold for a positive determination of a pathogenic infection, based upon the concentration of the reticulocyte bodies within the bodily sample.

11. The apparatus according to claim 1, wherein the at least one computer processor is configured to classify a pathogenic infection in the bodily sample as containing one or more given types of pathogen, by processing the candidate-informative feature in combination with the sample-informative feature.

12. The apparatus according to claim 11, wherein the at least one computer processor is configured to classify the pathogenic infection in the bodily sample as containing one or more given types of pathogen by classifying the pathogenic infection as containing one or more categories of pathogen selected from the group consisting of: *Plasmodium*, a given strain of *Plasmodium, Plasmodium* of a given age, and *Plasmodium* of a given age range.

13. The apparatus according to claim 11, wherein:
the at least one computer processor is configured to extract, from the one or more images, at least one sample-informative feature that is indicative of contextual information related to the bodily sample by extracting, from the one or more images, the relationship between the number of reticulocytes associated with candidates and the number of mature red blood cells associated with candidates; and
the at least one computer processor is configured to classify the pathogenic infection in the bodily sample as containing one or more given types of pathogen by classifying the pathogenic infection in the bodily sample as containing the given type of pathogen, at least partially based upon the relationship between the number of reticulocytes associated with candidates and the number of mature red blood cells associated with candidates.

14. A method comprising:
acquiring one or more microscope images of a bodily sample, using a microscope, the bodily sample being selected from the group consisting of: a blood sample, a diluted blood sample, a sample comprising predominantly red blood cells, and a diluted sample comprising predominantly red blood cells;
using at least one computer processor:
in the one or more images, identifying at least one element as being a pathogen candidate;
extracting, from the one or more images, at least one candidate-informative feature associated with the pathogen candidate;
extracting, from the one or more images, at least one sample-informative feature that is indicative of contextual information related to the bodily sample, the sample-informative feature being selected from the group consisting of: an indication of a presence of Howell Jolly bodies within the bodily sample, a concentration of platelets within the bodily sample, a relationship between a number of reticulocytes associated with candidates and a number of mature red blood cells associated with candidates, and a concentration of reticulocyte bodies within the bodily sample;
determining a likelihood of the bodily sample being infected with a pathogenic infection, by processing the candidate-informative feature in combination with the sample-informative feature; and
generating an output, in response thereto.

15. The method according to claim 14, wherein:
acquiring one or more microscope images of the selected bodily sample comprises acquiring one or more microscope images of a bodily sample that is stained with a stain; and
identifying at least one element as being a pathogen candidate comprises identifying the at least one element as being a pathogen candidate by identifying that the at least one element is stained.

16. The method according to claim 14, wherein processing the candidate-informative feature in combination with the sample-informative feature comprises:
in response to the candidate-informative feature, performing a first determining step, in which a likelihood of the pathogen candidate being a pathogen is determined; and
in response to the first determining step in combination with the sample-informative feature, performing a second determining step in which a likelihood of the bodily sample containing a pathogenic infection is determined.

17. The method according to claim 14, wherein processing the candidate-informative feature in combination with the sample-informative feature comprises:
in response to the candidate-informative feature in combination with the sample-informative feature, performing a first determining step, in which a likelihood of the pathogen candidate being a pathogen is determined; and
at least partially in response to the first determining step, performing a second determining step in which in which a likelihood of the bodily sample containing a pathogenic infection is determined.

18. The method according to claim 14, wherein extracting, from the one or more images, at least one candidate-informative feature associated with the pathogen candidate comprises extracting, from the one or more images, at least one candidate-informative feature associated with the pathogen candidate, the candidate-informative feature being a feature selected from the group consisting of: a size of the pathogen candidate, a shape of the pathogen candidate, a motion of the pathogen candidate, an intensity of the pathogen candidate, a location of the pathogen candidate within the bodily sample, a property of a cell overlapping the pathogen candidate, a color of the pathogen candidate, a texture of the pathogen candidate, and a sharpness of a boundary of the pathogen candidate.

19. The method according to claim 14, wherein extracting, from the one or more images, at least one sample-informative feature that is indicative of contextual information related to the bodily sample comprises extracting, from the one or more images, the indication of the presence of Howell Jolly bodies within the bodily sample.

20. The method according to claim 14, wherein extracting, from the one or more images, at least one sample-informative feature that is indicative of contextual information related to the bodily sample comprises extracting, from the one or more images, the concentration of platelets within the bodily sample.

21. The method according to claim 14, wherein extracting, from the one or more images, at least one sample-informative feature that is indicative of contextual information related to the bodily sample comprises extracting, from the one or more images, the relationship between the number of reticulocytes associated with candidates and the number of mature red blood cells associated with candidates.

22. The method according to claim 14, wherein extracting, from the one or more images, at least one sample-informative feature that is indicative of contextual information related to the bodily sample comprises extracting, from the one or more images, the concentration of reticulocyte bodies within the bodily sample.

23. The method according to claim 22, wherein determining the likelihood of the bodily sample being infected with the pathogenic infection comprises adjusting a threshold for a positive determination of a pathogenic infection, based upon the concentration of the reticulocyte bodies within the bodily sample.

24. The method according to claim 14, further comprising classifying a pathogenic infection in the bodily sample as containing one or more given types of pathogen, by processing the candidate-informative feature in combination with the sample-informative feature.

25. The method according to claim 24, wherein classifying the pathogenic infection in the bodily sample as containing the one or more given types of pathogenic infection comprises classifying the pathogenic infection as containing one or more categories of pathogen selected from the group consisting of: *Plasmodium*, a given strain of *Plasmodium*, *Plasmodium* of a given age, and *Plasmodium* of a given age range.

26. The method according to claim 24, wherein
extracting, from the one or more images, at least one sample-informative feature that is indicative of contextual information related to the bodily sample comprises extracting, from the one or more images, the relationship between the number of reticulocytes associated with candidates and the number of mature red blood cells associated with candidates, and
classifying the pathogenic infection in the bodily sample as containing the given type of pathogen comprises classifying the pathogenic infection in the bodily sample as containing the given type of pathogen, at least partially based upon the relationship between the number of reticulocytes associated with candidates and the number of mature red blood cells associated with candidates.

27. A computer software product, for use with a bodily sample, an output device, and a microscope system configured to acquire one or more microscope images of a bodily sample selected from the group consisting of: a blood sample, a diluted blood sample, a sample comprising predominantly red blood cells, and a diluted sample comprising predominantly red blood cells, the computer software product comprising a non-transitory computer-readable medium in which program instructions are stored, which instructions, when read by a computer cause the computer to perform the steps of: in the one or more images, identifying at least one element as being a pathogen candidate; extracting, from the one or more images, at least one candidate-informative feature associated with the pathogen candidate; extracting, from the one or more images, at least one sample-informative feature that is indicative of contextual information related to the bodily sample the sample-informative feature being selected from the group consisting of: an indication of a presence of Howell Jolly bodies within the bodily sample, a concentration of platelets within the bodily sample, a relationship between a number of reticulocytes associated with candidates and a number of mature red blood cells associated with candidates, and a concentration of reticulocyte bodies within the bodily sample; determining a likelihood of the bodily sample being infected with a pathogenic infection, by processing the candidate-informative feature in combination with the sample-informative feature; and generating an output upon the output device, in response thereto.

* * * * *